United States Patent
Mogensen et al.

(10) Patent No.: US 8,162,892 B2
(45) Date of Patent: Apr. 24, 2012

(54) INJECTOR DEVICE FOR PLACING A SUBCUTANEOUS INFUSION SET

(75) Inventors: Lasse Wesseltoft Mogensen, Søborg (DK); Grete Kornerup, Ringsted (DK); Magnus Walter Göransson, Malmö (SE)

(73) Assignee: Unomedical A/S, Birkeroed (DK)

( * ) Notice: Subject to any disclaimer, the term of this patent is extended or adjusted under 35 U.S.C. 154(b) by 1600 days.

(21) Appl. No.: 10/813,214

(22) Filed: Mar. 29, 2004

(65) Prior Publication Data

US 2005/0043687 A1 Feb. 24, 2005

Related U.S. Application Data

(63) Continuation of application No. 10/687,568, filed on Oct. 15, 2003, which is a continuation-in-part of application No. PCT/DK02/00640, filed on Sep. 27, 2002, which is a continuation-in-part of application No. 09/995,237, filed on Nov. 26, 2001, now Pat. No. 6,830,562, which is a continuation-in-part of application No. 09/967,400, filed on Sep. 28, 2001, now abandoned.

(30) Foreign Application Priority Data

Sep. 27, 2001 (DK) .......................... PA 2001 01411

(51) Int. Cl.
*A61M 5/20* (2006.01)
*A61M 5/178* (2006.01)
*A61M 5/32* (2006.01)

(52) U.S. Cl. .................. 604/165.01; 604/157; 604/192

(58) Field of Classification Search .............. 604/93.01, 604/164.01, 164.12, 156–158, 136–138, 604/164.08, 192–198, 263

See application file for complete search history.

(56) References Cited

U.S. PATENT DOCUMENTS 643,544 A 2/1900 Simmons
(Continued)

FOREIGN PATENT DOCUMENTS

DE 893 296 12/1953
(Continued)

OTHER PUBLICATIONS

Japanese Office Action mailed Jun. 15, 2009 for Japanese Patent Application No. 2003-530539, with English translation.

*Primary Examiner* — Kevin C Sirmons
*Assistant Examiner* — Andrew Gilbert
(74) *Attorney, Agent, or Firm* — Brinks Hofer Gilson & Lione

(57) ABSTRACT

An injector device assembly and a method for making an injector device assembly are provided. The injector assembly includes a sterile insertion set with a housing and a hollow cannula and a device housing. A plunger is slidably received within the device housing for movement between an advanced position and a retracted position wherein the cannula is transcutaneously placed upon movement of the plunger from the advanced position to the retracted position. The device housing has a forward end defining a surface of placement against the skin of a patient with the device housing in a predetermined orientation relative to the patient's skin. The injector device assembly includes a spring for urging the plunger toward the advanced position and a releasable cover member covering the forward end. The cover member and the device housing assure sterile conditions of the insertion set within the device housing prior to removal of the cover member.

51 Claims, 20 Drawing Sheets

U.S. PATENT DOCUMENTS

| | | | |
|---|---|---|---|
| 1,838,825 A | 1/1929 | Goldstein | |
| 1,991,103 A | 2/1935 | King | |
| 2,047,010 A | 7/1936 | Dickinson | |
| 2,295,849 A | 9/1942 | Kayden | |
| 2,319,731 A | 5/1943 | Garrett | |
| 2,533,731 A | 12/1950 | Gomberg | |
| 2,630,803 A | 3/1953 | Baran | |
| 2,690,529 A | 9/1954 | Lindblad | |
| 2,730,099 A | 1/1956 | Sullivan | |
| 2,839,060 A | 6/1958 | Ormo | |
| 2,936,141 A | 5/1960 | Rapata | |
| 2,952,420 A | 9/1960 | Von Hoorn | |
| 3,055,361 A | 9/1962 | Ballard | |
| 3,074,541 A | 1/1963 | Roehr | |
| 3,107,785 A | 10/1963 | Roehr | |
| 3,154,080 A | 10/1964 | Rowan et al. | |
| 3,317,166 A | 5/1967 | Janssen | |
| 3,545,286 A | 12/1970 | Stenstrom | |
| 3,547,119 A | 12/1970 | Hall et al. | |
| 3,610,240 A | 10/1971 | Harautuneian | |
| 3,648,999 A | 3/1972 | Bauer | |
| 3,783,996 A | 1/1974 | Gerard et al. | |
| 3,814,097 A | 6/1974 | Ganderton et al. | |
| 3,831,729 A | 8/1974 | Howard | |
| 3,840,011 A | 10/1974 | Wright | |
| 3,865,236 A | 2/1975 | Rycroft | |
| 3,937,219 A * | 2/1976 | Karakashian | 604/26 |
| 3,942,528 A | 3/1976 | Loeser | |
| 3,986,508 A | 10/1976 | Barrington | |
| 4,014,328 A | 3/1977 | Cluff et al. | |
| 4,022,205 A | 5/1977 | Tenczar | |
| 4,146,113 A | 3/1979 | Gavel | |
| 4,150,798 A | 4/1979 | Aragon | |
| 4,188,950 A | 2/1980 | Wardlaw | |
| 4,201,406 A | 5/1980 | Dennehey et al. | |
| 4,227,528 A | 10/1980 | Wardlaw | |
| 4,267,836 A | 5/1981 | Whitney et al. | |
| 4,306,705 A | 12/1981 | Svenson | |
| 4,315,505 A | 2/1982 | Crandall et al. | |
| 4,334,551 A | 6/1982 | Pfister | |
| D267,199 S | 12/1982 | Koenig | |
| 4,365,630 A | 12/1982 | McFlarlane | |
| 4,400,861 A | 8/1983 | Parker | |
| 4,406,042 A | 9/1983 | McPhee | |
| 4,458,344 A | 7/1984 | Coogler | |
| 4,472,024 A | 9/1984 | Konomura et al. | |
| 4,473,369 A | 9/1984 | Lueders et al. | |
| 4,500,312 A | 2/1985 | McFarlane | |
| 4,517,971 A | 5/1985 | Sorbonned | |
| 4,530,695 A | 7/1985 | Phillips et al. | |
| 4,531,686 A | 7/1985 | Shaw | |
| 4,531,937 A | 7/1985 | Yates | |
| 4,563,177 A | 1/1986 | Kamen | |
| 4,576,846 A | 3/1986 | Noel | |
| 4,606,735 A | 8/1986 | Wilder et al. | |
| 4,610,469 A | 9/1986 | Wolff-Mooij | |
| 4,616,790 A | 10/1986 | Beltran | |
| 4,619,349 A | 10/1986 | Braun | |
| 4,635,683 A | 1/1987 | Nielsen | |
| 4,637,404 A | 1/1987 | Gessman | |
| 4,662,873 A | 5/1987 | Lash et al. | |
| 4,682,702 A | 7/1987 | Gach | |
| 4,713,059 A | 12/1987 | Bickelhaupt et al. | |
| 4,734,092 A | 3/1988 | Millerd | |
| 4,755,173 A | 7/1988 | Konopka et al. | |
| 4,758,020 A | 7/1988 | Boyd | |
| 4,800,629 A | 1/1989 | Ikeda | |
| 4,802,638 A | 2/1989 | Burger et al. | |
| 4,817,603 A * | 4/1989 | Turner et al. | 606/182 |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,878,897 A | 11/1989 | Katzin | |
| 4,894,054 A * | 1/1990 | Miskinyar | 604/136 |
| 4,895,570 A | 1/1990 | Larkin | |
| D306,500 S | 3/1990 | Brahler | |
| 4,913,369 A | 4/1990 | Lia et al. | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olsen | |
| 5,024,662 A | 6/1991 | Menes et al. | |
| 5,067,496 A | 11/1991 | Eisele | |
| 5,077,872 A | 1/1992 | Guthammar | |
| 5,083,757 A | 1/1992 | Barsky | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | Van den Haak | |
| 5,116,324 A | 5/1992 | Brierley et al. | |
| 5,116,325 A | 5/1992 | Paterson | |
| 5,121,751 A | 6/1992 | Panalletta | |
| 5,129,884 A | 7/1992 | Dysarz | |
| 5,134,593 A | 7/1992 | Logan et al. | |
| 5,134,594 A | 7/1992 | Woo | |
| 5,137,516 A | 8/1992 | Rand et al. | |
| 5,137,524 A | 8/1992 | Lynn et al. | |
| 5,141,496 A | 8/1992 | Dalto et al. | |
| 5,147,319 A | 9/1992 | Ishikawa et al. | |
| 5,147,375 A | 9/1992 | Sullivan et al. | |
| 5,161,681 A | 11/1992 | Kemp et al. | |
| 5,163,915 A | 11/1992 | Holleron | |
| 5,176,650 A | 1/1993 | Haining | |
| 5,176,662 A | 1/1993 | Bartholomew et al. | |
| 5,188,314 A | 2/1993 | Peters | |
| 5,188,611 A | 2/1993 | Orgain | |
| RE34,223 E | 4/1993 | Bonaldo | |
| 5,222,947 A | 6/1993 | D'Amico | |
| 5,232,454 A | 8/1993 | Hollister | |
| 5,236,143 A | 8/1993 | Dragon | |
| 5,240,199 A | 8/1993 | Peters | |
| 5,248,301 A | 9/1993 | Koenig et al. | |
| 5,256,152 A | 10/1993 | Marks | |
| 5,257,980 A | 11/1993 | Van Antwerp et al. | |
| 5,265,822 A | 11/1993 | Shober, Jr. et al. | |
| 5,269,799 A | 12/1993 | Daniel | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,343,637 A | 9/1994 | Schindler | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,376,082 A | 12/1994 | Phelps | |
| 5,380,067 A | 1/1995 | Turvill et al. | |
| 5,384,174 A | 1/1995 | Ward et al. | |
| 5,387,197 A | 2/1995 | Smith et al. | |
| 5,388,931 A | 2/1995 | Carlson | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,429,607 A | 7/1995 | McPhee | |
| 5,429,613 A | 7/1995 | D'Amico | |
| 5,433,307 A | 7/1995 | Jeppe | |
| D362,718 S | 9/1995 | Deily et al. | |
| 5,449,349 A | 9/1995 | Sallee et al. | |
| 5,451,210 A | 9/1995 | Kramer et al. | |
| 5,487,506 A | 1/1996 | Drummond et al. | |
| 5,490,841 A | 2/1996 | Landis | |
| 5,492,313 A | 2/1996 | Pan et al. | |
| 5,505,709 A | 4/1996 | Funderburk et al. | |

| | | | | | | |
|---|---|---|---|---|---|---|
| 5,507,730 A | 4/1996 | Haber et al. | | 6,105,218 A | 8/2000 | Reekie |
| 5,519,167 A | 5/1996 | Kunimoto et al. | | 6,120,482 A | 9/2000 | Szabo |
| 5,520,654 A | 5/1996 | Wahlberg | | 6,123,690 A | 9/2000 | Mejslov |
| 5,522,803 A | 6/1996 | Teisson-Simony | | 6,132,755 A | 10/2000 | Eicher et al. |
| 5,533,974 A | 7/1996 | Gaba | | 6,159,181 A | 12/2000 | Crossman et al. |
| 5,540,709 A | 7/1996 | Ramel | | 6,183,464 B1 | 2/2001 | Sharp et al. |
| 5,545,143 A | 8/1996 | Fischell | | 6,191,338 B1 | 2/2001 | Haller |
| 5,545,152 A | 8/1996 | Funderburk et al. | | 6,193,694 B1 | 2/2001 | Bell et al. |
| 5,554,130 A | 9/1996 | McDonald et al. | | 6,219,574 B1 | 4/2001 | Cormier et al. |
| 5,558,650 A | 9/1996 | McPhee | | 6,221,058 B1 | 4/2001 | Kao et al. |
| 5,562,636 A | 10/1996 | Utterberg | | 6,248,093 B1 | 6/2001 | Moberg |
| 5,575,777 A | 11/1996 | Cover et al. | | 6,293,925 B1 * | 9/2001 | Safabash et al. ............... 604/136 |
| 5,584,813 A | 12/1996 | Livingston et al. | | 6,302,866 B1 | 10/2001 | Marggi |
| 5,591,188 A | 1/1997 | Waisman | | 6,319,232 B1 | 11/2001 | Kashmer |
| 5,599,309 A | 2/1997 | Marshall et al. | | 6,322,535 B1 | 11/2001 | Hitchins et al. |
| 5,599,315 A | 2/1997 | McPhee | | 6,322,808 B1 | 11/2001 | Trautman et al. |
| 5,599,318 A | 2/1997 | Sweeney et al. | | 6,334,856 B1 | 1/2002 | Allen et al. |
| 5,628,765 A | 5/1997 | Morita | | 6,355,021 B1 | 3/2002 | Nielsen et al. |
| 5,643,214 A | 7/1997 | Marshall | | 6,379,335 B1 | 4/2002 | Rigon et al. |
| 5,643,216 A | 7/1997 | White | | D456,692 S | 5/2002 | Epstein |
| 5,643,220 A | 7/1997 | Cosme | | 6,387,076 B1 | 5/2002 | Van Lunduyt |
| 5,662,617 A | 9/1997 | Odell et al. | | 6,450,992 B1 | 9/2002 | Cassidy, Jr. |
| 5,665,071 A | 9/1997 | Wyrick | | 6,488,663 B1 | 12/2002 | Steg |
| 5,665,075 A | 9/1997 | Gyure et al. | | 6,517,517 B1 | 2/2003 | Farrugia et al. |
| 5,676,156 A | 10/1997 | Yoon | | 6,520,938 B1 | 2/2003 | Funderburk et al. |
| 5,681,323 A | 10/1997 | Arick | | D472,316 S | 3/2003 | Douglas et al. |
| 5,695,476 A | 12/1997 | Harris | | D472,630 S | 4/2003 | Douglas et al. |
| 5,704,920 A | 1/1998 | Gyure | | 6,572,586 B1 | 6/2003 | Wojcik |
| 5,709,516 A | 1/1998 | Peterson et al. | | 6,579,267 B2 | 6/2003 | Lynch et al. |
| 5,714,225 A | 2/1998 | Hansen et al. | | 6,582,397 B2 | 6/2003 | Alesi et al. |
| 5,738,641 A | 4/1998 | Watson et al. | | 6,595,962 B1 | 7/2003 | Perthu |
| 5,741,288 A | 4/1998 | Rife | | 6,607,509 B2 | 8/2003 | Bobroff et al. |
| 5,752,923 A | 5/1998 | Terwilliger | | 6,620,136 B1 | 9/2003 | Pressly, Sr. et al. |
| 5,807,316 A * | 9/1998 | Teeple, Jr. ..................... 604/506 | | 6,629,949 B1 | 10/2003 | Douglas |
| 5,810,835 A | 9/1998 | Ryan et al. | | 6,645,182 B1 | 11/2003 | Szabo |
| 5,817,058 A | 10/1998 | Shaw | | 6,685,674 B2 | 2/2004 | Douglas et al. |
| 5,820,598 A | 10/1998 | Gazza et al. | | 6,702,779 B2 | 3/2004 | Connelly et al. |
| 5,833,666 A | 11/1998 | Davis et al. | | 6,726,649 B2 | 4/2004 | Swenson et al. |
| D402,538 S | 12/1998 | Wagter et al. | | 6,736,797 B1 | 5/2004 | Larsen et al. |
| 5,843,001 A | 12/1998 | Goldenberg | | 6,749,589 B1 | 6/2004 | Douglas et al. |
| 5,848,990 A | 12/1998 | Cirelli et al. | | 6,790,199 B1 | 9/2004 | Gianakos |
| 5,851,197 A | 12/1998 | Marano et al. | | 6,805,686 B1 | 10/2004 | Fathallah et al. |
| 5,858,001 A | 1/1999 | Tsals et al. | | 6,811,545 B2 | 11/2004 | Vaillancourt |
| 5,865,806 A | 2/1999 | Howell | | 6,814,720 B2 | 11/2004 | Olsen et al. |
| 5,873,540 A | 2/1999 | Hardin | | 6,824,530 B2 | 11/2004 | Wagner et al. |
| 5,899,886 A | 5/1999 | Cosme | | 6,824,531 B1 | 11/2004 | Zecha, Jr. et al. |
| 5,913,846 A | 6/1999 | Szabo | | 6,830,562 B2 | 12/2004 | Mogensen et al. |
| 5,915,640 A | 6/1999 | Wagter et al. | | 6,837,877 B2 | 1/2005 | Zurcher |
| 5,919,167 A | 7/1999 | Mulhauser et al. | | 6,840,922 B2 | 1/2005 | Nielsen et al. |
| 5,925,032 A | 7/1999 | Clements | | 6,880,701 B2 | 4/2005 | Bergeron et al. |
| 5,947,931 A | 9/1999 | Bierman | | 6,916,017 B2 | 7/2005 | Noe |
| 5,947,935 A | 9/1999 | Rhinehart et al. | | 6,923,791 B2 | 8/2005 | Douglas |
| 5,951,523 A | 9/1999 | Osterlind et al. | | 6,926,694 B2 | 8/2005 | Marano-Ford et al. |
| 5,954,643 A | 9/1999 | VanAntwerp et al. | | 6,939,331 B2 | 9/2005 | Ohshima |
| 5,957,892 A | 9/1999 | Thorne | | 6,949,084 B2 | 9/2005 | Marggi et al. |
| 5,968,011 A | 10/1999 | Larsen et al. | | 7,018,344 B2 | 3/2006 | Bressler et al. |
| 5,975,120 A | 11/1999 | Novosel | | 7,056,302 B2 | 6/2006 | Douglas |
| 5,980,488 A | 11/1999 | Thorne | | 2001/0004970 A1 | 6/2001 | Hollister et al. |
| 5,980,506 A | 11/1999 | Mathiasen | | 2001/0016714 A1 | 8/2001 | Bell et al. |
| 5,984,224 A | 11/1999 | Yang | | 2001/0021827 A1 | 9/2001 | Ferguson et al. |
| 5,984,897 A | 11/1999 | Peterson et al. | | 2001/0039401 A1 | 11/2001 | Ferguson et al. |
| 5,992,787 A | 11/1999 | Burke | | 2001/0041875 A1 | 11/2001 | Higuchi et al. |
| D417,733 S | 12/1999 | Howell et al. | | 2002/0022855 A1 | 2/2002 | Bobroff et al. |
| 6,017,328 A | 1/2000 | Fischell et al. | | 2002/0068904 A1 | 6/2002 | Pluth et al. |
| D421,119 S | 2/2000 | Musgrave et al. | | 2002/0072720 A1 | 6/2002 | Hague et al. |
| 6,039,629 A | 3/2000 | Mitchell | | 2002/0077599 A1 | 6/2002 | Wojcik |
| 6,042,570 A | 3/2000 | Bell et al. | | 2002/0082543 A1 | 6/2002 | Park et al. |
| 6,045,533 A | 4/2000 | Kriesel et al. | | 2002/0107489 A1 | 8/2002 | Lee |
| 6,050,976 A | 4/2000 | Thorne et al. | | 2002/0111581 A1 | 8/2002 | Sasso |
| 6,056,718 A | 5/2000 | Funderburk et al. | | 2002/0145073 A1 | 10/2002 | Swanson |
| 6,056,726 A | 5/2000 | Isaacson | | 2002/0156424 A1 | 10/2002 | Suzuki et al. |
| 6,074,371 A | 6/2000 | Fischell | | 2002/0156427 A1 | 10/2002 | Suzuki et al. |
| 6,077,244 A | 6/2000 | Botich et al. | | 2002/0161332 A1 | 10/2002 | Ramey |
| 6,086,008 A | 7/2000 | Gray et al. | | 2002/0169419 A1 | 11/2002 | Steg |
| 6,086,575 A | 7/2000 | Mejslov | | 2002/0173748 A1 | 11/2002 | McConnell et al. |
| 6,090,068 A | 7/2000 | Chanut | | 2002/0173769 A1 | 11/2002 | Gray et al. |
| 6,093,172 A * | 7/2000 | Funderburk et al. .......... 604/135 | | 2002/0183688 A1 | 12/2002 | Lastovich et al. |
| 6,093,179 A | 7/2000 | O'Hara et al. | | 2002/0189688 A1 | 12/2002 | Roorda |
| 6,099,503 A | 8/2000 | Stradella | | 2002/0193737 A1 | 12/2002 | Popovsky |

| Publication No. | Date | Inventor |
|---|---|---|
| 2002/0193744 A1 | 12/2002 | Alesi et al. |
| 2003/0014018 A1 | 1/2003 | Giambattista et al. |
| 2003/0069548 A1 | 4/2003 | Connelly et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0199123 A1 | 10/2004 | Nielsen |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0043687 A1 | 2/2005 | Mogensen et al. |
| 2005/0075606 A1 | 4/2005 | Botich et al. |
| 2005/0101910 A1 | 5/2005 | Bowman et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119637 A1 | 6/2005 | Lundgren et al. |
| 2005/0124936 A1 | 6/2005 | Mogensen et al. |
| 2005/0159709 A1 | 7/2005 | Wilkinson |
| 2005/0215979 A1 | 9/2005 | Konerup et al. |
| 2005/0251098 A1 | 11/2005 | Wyss et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0030815 A1 | 2/2006 | Csincsura et al. |
| 2006/0041224 A1 | 2/2006 | Jensen |
| 2006/0173413 A1 | 8/2006 | Fan |

FOREIGN PATENT DOCUMENTS

| | | |
|---|---|---|
| DE | 1 053 541 | 3/1959 |
| DE | 26 20 009 A1 | 12/1977 |
| DE | 28 03 509 | 8/1979 |
| DE | 37 22 893 C1 | 6/1988 |
| DE | 38 23 447 | 2/1996 |
| DE | 196 31 921 | 3/1997 |
| DE | 196 10 692 A1 | 9/1997 |
| DE | 299 05 072 U1 | 9/1999 |
| DE | 298 18 311 U1 | 11/1999 |
| DE | 198 47 143 A1 | 1/2000 |
| DE | 101 06 074 A1 | 9/2000 |
| DE | 100 49 001 A1 | 4/2002 |
| DE | 299 21 406 U1 | 11/2002 |
| DE | 203 20 207 U1 | 11/2004 |
| EP | 0 188 014 B1 | 10/1985 |
| EP | 0 239 244 B1 | 2/1987 |
| EP | 0 290 176 A1 | 11/1988 |
| EP | 0 298 521 B1 | 9/1990 |
| EP | 0 451 040 A1 | 10/1991 |
| EP | 0 184 231 B1 | 1/1992 |
| EP | 0 475 857 | 3/1992 |
| EP | 0 544 837 B1 | 6/1993 |
| EP | 0 633 039 | 7/1994 |
| EP | 0 651 662 B1 | 5/1995 |
| EP | 0 657 184 A1 | 6/1995 |
| EP | 0 714 631 B1 | 6/1996 |
| EP | 744 183 A2 | 11/1996 |
| EP | 0 747 006 A1 | 12/1996 |
| EP | 0 799 626 A1 | 10/1997 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0 956 879 A1 | 11/1999 |
| EP | 0 615 768 A2 | 12/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |
| EP | 1 167 765 A2 | 1/2002 |
| EP | 0 775 501 | 6/2002 |
| EP | 0 894 216 B1 | 7/2003 |
| EP | 1 329 233 A1 | 7/2003 |
| EP | 1 360 970 A1 | 11/2003 |
| EP | 1 380 315 A1 | 1/2004 |
| EP | 1 475 113 A1 | 11/2004 |
| FR | 576 849 | 8/1924 |
| FR | 2 611 013 | 8/1988 |
| FR | 2725902 | 10/1994 |
| FR | 2 733 915 | 11/1996 |
| FR | 2 781 617 A1 | 1/2000 |
| GB | 591730 | 3/1946 |
| GB | 906574 | 9/1962 |
| GB | 1 268 575 | 3/1972 |
| GB | 1 403 034 | 8/1975 |
| GB | 2 088 215 A | 6/1982 |
| GB | 2 224 808 A | 5/1990 |
| GB | 2 270 552 A | 3/1994 |
| JP | A-03-191965 A | 8/1991 |
| JP | 05326062 A | 12/1993 |
| JP | 7051251 | 11/1995 |
| JP | A-08-187286 A | 7/1996 |
| JP | 9217584 A | 9/1997 |
| JP | 10-15075 A | 1/1998 |
| JP | A-10-179734 A | 7/1998 |
| JP | 3140740 | 2/2000 |
| JP | 2000059877 A | 2/2000 |
| JP | 2002-028246 | 1/2002 |
| NL | 1017427 C | 11/2002 |
| WO | WO 81/01795 A1 | 7/1981 |
| WO | WO 82/03558 A1 | 10/1982 |
| WO | WO 87/06474 | 11/1987 |
| WO | WO 9204062 A1 | 3/1992 |
| WO | WO 93/03787 | 3/1993 |
| WO | WO 93/05840 | 4/1993 |
| WO | WO 94/20160 | 9/1994 |
| WO | WO 95/28327 A | 10/1995 |
| WO | WO 96/20021 A1 | 7/1996 |
| WO | WO 96/32981 A1 | 10/1996 |
| WO | WO 96/35472 A1 | 11/1996 |
| WO | WO 98/09065 | 3/1998 |
| WO | WO 98/58693 | 12/1998 |
| WO | WO 99/07435 | 2/1999 |

| | | | | | | |
|---|---|---|---|---|---|---|
| WO | WO 99/33504 | 7/1999 | | WO | WO 02/066854 A1 | 8/2002 |
| WO | WO 99/36009 | 7/1999 | | WO | WO 02/068014 | 9/2002 |
| WO | WO 99/56802 | 11/1999 | | WO | WO 02/081012 A2 | 10/2002 |
| WO | WO 99/61815 | 12/1999 | | WO | WO 02/094352 | 11/2002 |
| WO | WO 00/02614 | 1/2000 | | WO | WO 02/100457 | 12/2002 |
| WO | WO 00/03757 | 1/2000 | | WO | WO 02/102442 A1 | 12/2002 |
| WO | WO 00/44324 A1 | 8/2000 | | WO | WO 03/015860 A1 | 2/2003 |
| WO | WO 01/04507 A1 | 1/2001 | | WO | WO 03/026728 | 4/2003 |
| WO | WO 01/30419 A2 | 5/2001 | | WO | WO 2004/030726 A | 4/2004 |
| WO | WO 01/68180 | 9/2001 | | WO | WO 2004/087240 | 10/2004 |
| WO | WO 01/72353 A2 | 10/2001 | | WO | WO 2005/004973 | 1/2005 |
| WO | WO 01/81785 A1 | 11/2001 | | WO | WO 2005/046780 A1 | 5/2005 |
| WO | WO 01/93926 A2 | 12/2001 | | WO | WO 2005/068006 A1 | 7/2005 |
| WO | WO 02/46080 | 6/2002 | | | | |

* cited by examiner

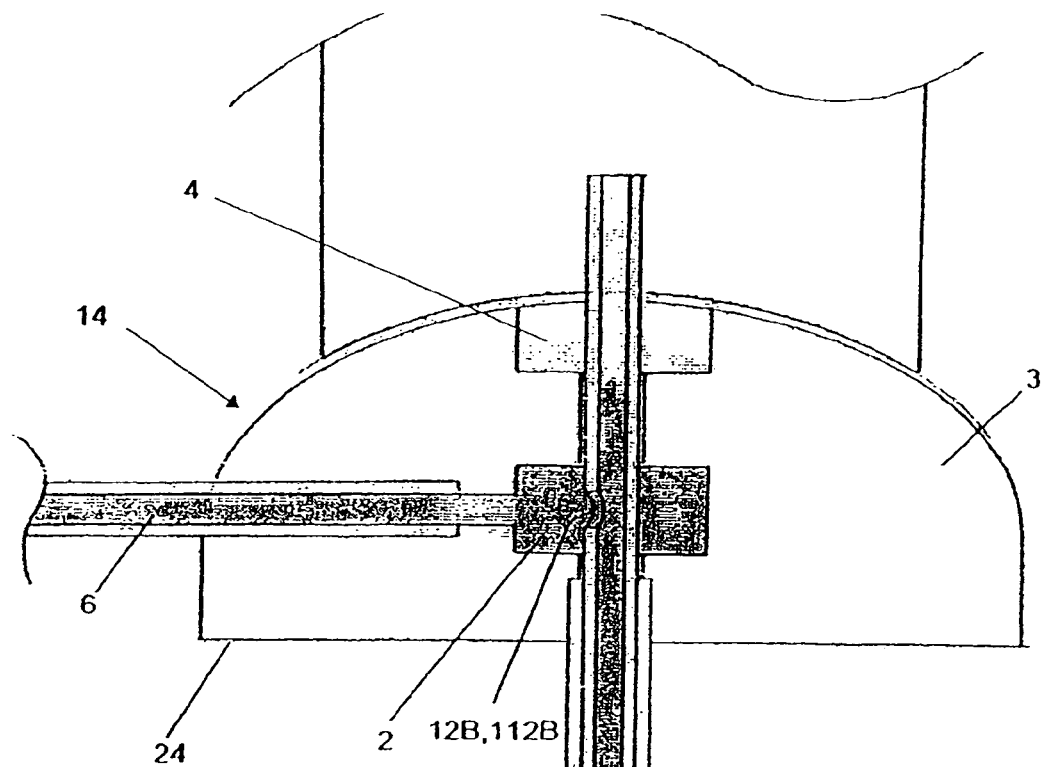
Fig. 18
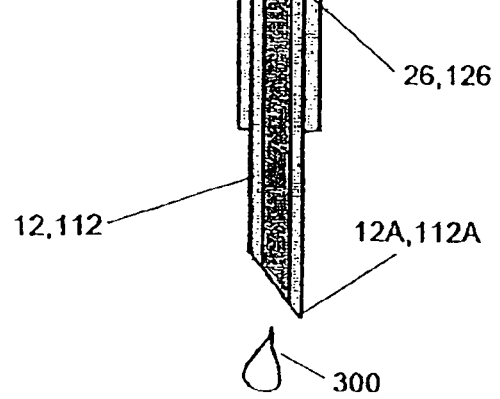

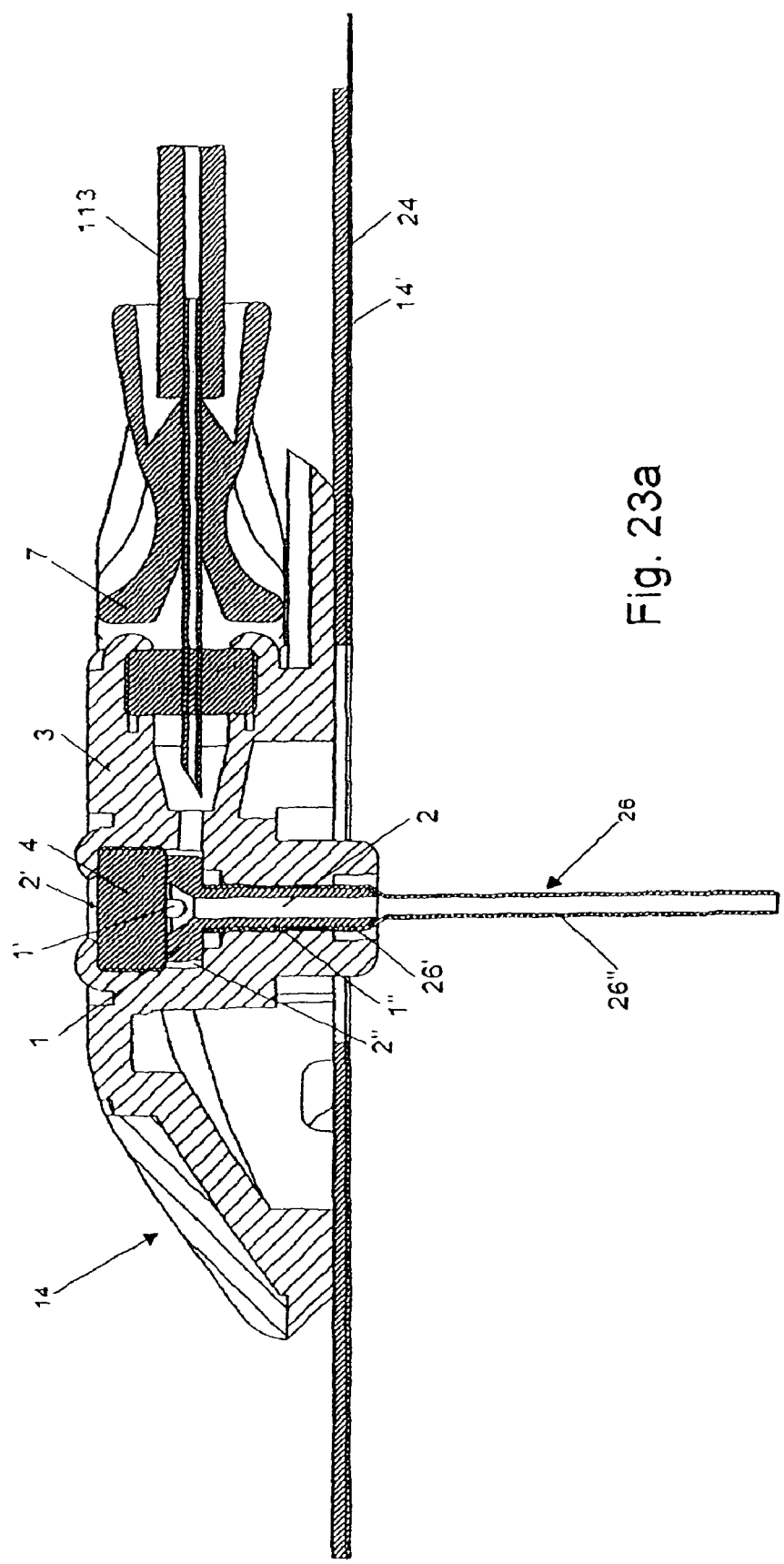

INJECTOR DEVICE FOR PLACING A SUBCUTANEOUS INFUSION SET

BACKGROUND OF THE INVENTION

This application is a continuation of U.S. application Ser. No. 10/687,568, filed Oct. 15, 2003, which is a continuation-in-part of PCT/DK02/00640, filed Sep. 27, 2002 which is a continuation-in-part of U.S. application Ser. No. 09/995,237, filed Nov. 26, 2001, now U.S. Pat. No. 6,830,562, which is a continuation-in-part of U.S. application Ser. No. 09/967,400, filed Sep. 28, 2001 now abandoned and a continuation of Danish Patent Application No. PA 2001 01411 filed on Sep. 27, 2001, the entirety of these references are incorporated herein.

Medical needles are widely used in the course of patient treatment, particularly for delivery of selected medications. In one form, hollow hypodermic needles are employed for transcutaneous delivery of the medication from a syringe or the like, see U.S. Pat. No. 5,665,071. In another, as shown in U.S. Pat. No. 5,591,188 incorporated herein by reference, an insertion needle used in conjunction with an injector device is employed for transcutaneous placement of a soft and relatively flexible tubular cannula, followed by removal of the insertion needle and subsequent infusion of medical fluid to the patient through the cannula. U.S. Pat. No. 5,681,323 relates to an insertion device for an emergency cricothyrotomy tube.

It is often necessary for a patient to transcutaneously place the medical needle himself. For example, diabetic patients frequently place a subcutaneous infusion set with a cannula for subsequent programmable delivery of insulin by means of a medication infusion pump. Such subcutaneous infusion sets are disclosed, for example, in U.S. Pat. Nos. 4,755,173, 5,176,662, 5,257,980 and WO 98/58693 which are incorporated by reference herein.

Some patients are reluctant or hesitant to pierce their own skin with a medical needle, and thus encounter difficulties in correct needle placement for proper administration of the medication. Such difficulties can be attributable to insufficient manual skill to achieve proper needle placement or alternately to anxiety associated with anticipated discomfort as the needle pierces the skin. This problem can be especially significant with medications delivered via a subcutaneous infusion set, since incorrect placement can cause kinking of the cannula and resultant obstruction of medication flow to the patient Cannula kinking can be due to infusion set placement at an incorrect angle relative to the patient's skin, and/or needle placement with an incorrect force and speed of insertion.

The present invention is aimed at providing an improved injector device, which may allow for a shortening of the total time required for the placement of an infusion set. The present invention also aims at providing an improved spring-type drive for urging a plunger within a housing to an advanced position.

SUMMARY OF THE INVENTION

In accordance with the invention, an injector device has a plunger with a medical needle which may be hollow to allow for discharge of medication when priming the infusion set, and which is adapted for the quick and easy transcutaneous placement through the skin of a patient of the cannula of a subcutaneous infusion set, the insertion needle extending through the infusion set and protruding from the end of the cannula. The injector device is designed to place the cannula with the insertion needle extending therethrough, preferably with a controlled force and speed of insertion, to ensure proper needle placement with minimal patient discomfort The injector device may also allow placement of the insertion needle through the skin at a selected insertion angle. After priming and placement of the infusion set the injector device is removed and delivery of medication is initiated.

Preferably, the injector device is provided to the patient as a sterile sealed, single use assembly including a subcutaneous infusion set with a housing already mounted on the insertion needle of the injector device, thereby reducing the number of components to be handled by the patient prior to the placement of the subcutaneous infusion set. The injector device assembly may be designed such that no further packaging is required leading to substantial cost reductions.

More particularly, the injector device comprises a device housing, preferably having an elongated bore, and a plunger slidably received therein for movement between an advanced position and a retracted position, the plunger having substantially non detachably secured thereto an insertion needle adapted to receive and support said cannula in a position with the cannula oriented for transcutaneous placement upon movement of the plunger with said needle from the retracted position to the advanced position. A drive urges the plunger with a controlled force and speed from the retracted position toward the advanced position to transcutaneously place said cannula of said subcutaneous infusion set received on said insertion needle. The insertion needle on the plunger is removable from said cannula while maintaining the transcutaneous placement of the cannula. By "substantially non-detachably" as used in the present application is meant a connection, which will remain stable under normal conditions of use to allow the needle to remain on the plunger when retracting the injector device from a patient's skin.

Preferably, the injector comprises a spring-loaded plunger having a head for receiving the infusion set in a position with the insertion needle projecting outwardly for transcutaneous placement through the skin of a patient. A front end of the housing is designed for being pressed against the skin of a patient, at a selected needle insertion site; and in an orientation with the needle disposed at a correct or desired insertion angle. A trigger member is operable to release the plunger and thereby permit the drive spring to carry the infusion set toward the patient's skin with a controlled force and speed, resulting in proper transcutaneous placement of the insertion needle with minimal patient discomfort.

The invention also relates to a novel spring type drive for urging the plunger of an injector device to the advanced position, preferably for transcutaneously placing a subcutaneous infusion set, wherein the drive comprises a number of individual, elongated flexible plastics members, preferably extending around a respective part of the periphery of the plunger, in the annular space between the plunger and a device housing. Each member is connected with the plunger and with the device housing. In the advanced position of the plunger, the plastics members are essentially plane and non-deformed. However, when moving the plunger to the retracted position, the plastics members are bend, setting up the required force that seeks to drive the plunger to an advanced position. The novel spring type drive may also be implemented in injector devices of the type disclosed in U.S. Pat. Nos. 6,093,172, 5,851,197 and WO 99/133504 where the plunger head does not have an insertion needle mounted thereon for receiving an infusion set, but includes a recess adapted for receiving as well as supporting a subcutaneous infusion set.

BRIEF DESCRIPTION OF THE DRAWINGS

The accompanying drawings illustrate the invention.

FIG. 18 is a cross-sectional view showing how priming of an infusion set may be carried out using a hollow insertion needle.

FIG. 20e shows a side view of the injector device shown in FIG. 20a.

FIGS. 23a and 23b show a schematic cross sectional view through the infusion set of FIG. 17, without and with an insertion needle, respectively.

DETAILED DESCRIPTION OF THE PREFERRED EMBODIMENTS

Figure 1:
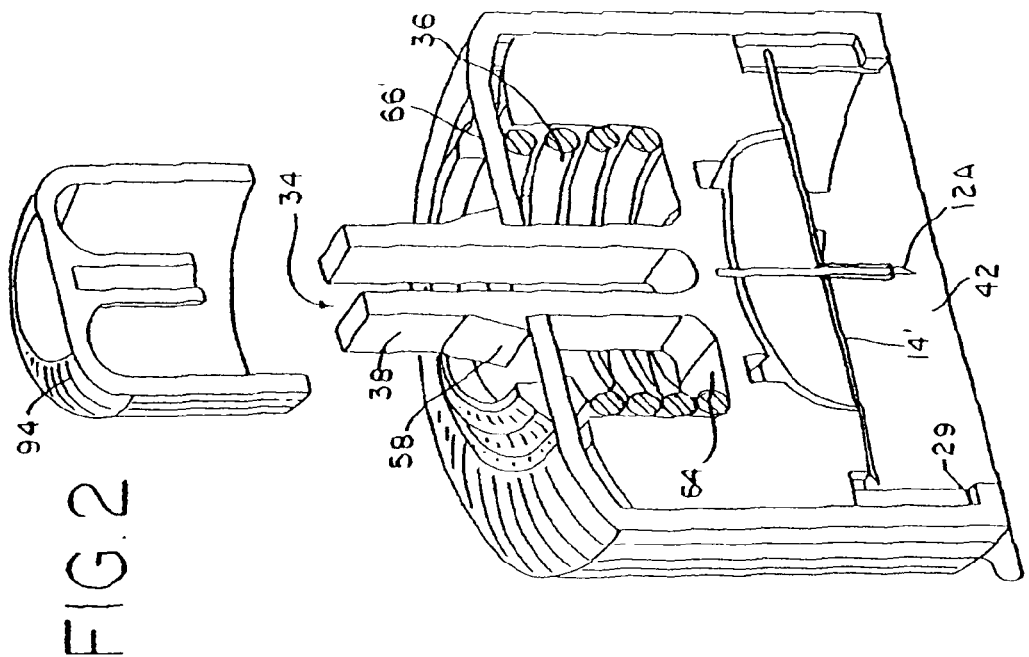
FIG. 1 is a perspective schematic vertical cross-sectional view illustrating an injector device embodying the novel features of the invention.

An injector device shown schematically in FIG. 1 by the reference numeral 10 is provided for quick and easy placement of a subcutaneous infusion set 14, and may then be discarded safely. The infusion set 14 with a cannula 26 extending therefrom is shown schematically only.

Figure 2:
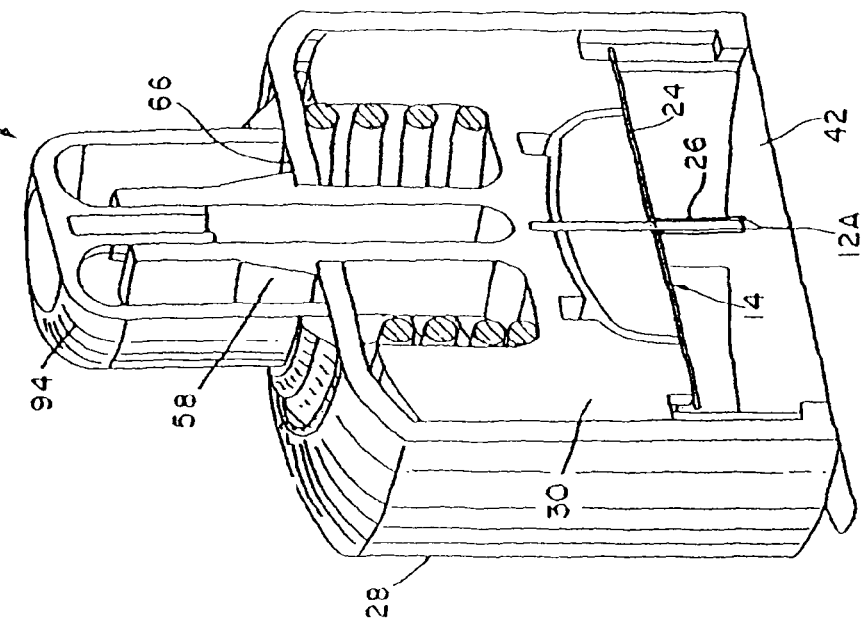
FIG. 2 is a schematic cross-sectional view of the injector device shown in FIG. 1, with the end cap removed.

The injector device 10 includes a plunger 30 having thereon a medical insertion needle 12 with a pointed end 12A. The plunger 30 is arranged for longitudinal sliding movement within a device housing 28 between a forward advanced position (FIGS. 3 and 4) and a rearward retracted position (FIGS. 1 and 2). The device housing 28 may have a circular, square or any desired cross-sectional shape. The device housing 28 and the plunger 30 are preferably formed of a plastics material in a moulding process.

The infusion set 14 is used to infuse medical fluids such as insulin to a patient, and generally includes a housing with an internal chamber (not shown) that receives medication via infusion tubing. An enlarged base 24 of the infusion set 14 is provided on the housing for stable affixation thereof to the skin of the patient. The enlarged base 24 may carry an adhesive and be provided with a release sheet 14' which is removed to expose the adhesive prior to placement of the infusion set. Alternatively, the base 24 may be sized to allow the infusion set to be fixed to the patient by an adhesive patch. The infusion set has a protruding soft and flexible cannula 26, which communicates with the internal chamber, and a passage sealed by a sealing membrane extends through the housing opposite the cannula 26. The medical insertion needle 12 of the injector device 10 extends through the passage, into the internal chamber and through the cannula 26, when the infusion set 14 is mounted in position on the injector device. After transcutaneous placement of the cannula 26, the injector device 10 with the insertion needle 12 is retracted from the infusion set 14 to permit medication delivery through the cannula 26 to the patient.

Examples of subcutaneous infusion sets suitable for use with the injector device of the present invention, and in particular in conjunction with the insertion needle of the injector device, are shown and described in U.S. Pat. Nos. 4,755,173, 5,176,662 and 5,257,980, European patent no 956 879 and in international patent application no: 98/58693, which are incorporated by reference herein. Such infusion sets generally include a hollow cannula part. The insertion needle shown in those publications may be obviated through the present invention Alternatively, the injector device according to the invention may be used to transcutaneously place a cannula associated with other types of infusion sets.

The invention provides a ready to use injector device, which may be molded from a suitable plastics material. An injector device assembly including the injector device and a subcutaneous infusion set will effectively simplify the placement of an infusion set as the assembly, as delivered from the factory, provides an infusion set already mounted on the insertion needle 12. The tune required for the placement of an infusion set is reduced.

The injector device 10 includes a trigger-type actuator mechanism for transcutaneous placement, with a controlled speed and force, of the insertion needle 12 which is secured to the plunger 30, with the insertion needle 12 oriented at an angular position relative to the skin of the patient in principally the manner as shown in international patent application no. 99/33504 incorporated herein by reference.

The plunger 30 has a recessed head 32 (FIG. 3) at a lower or forward end thereof shaped for receiving the housing of the subcutaneous infusion set 14. Centrally in the recess, the head 32 is provided with the metal insertion needle 12, which is securely connected thereto. The insertion needle 12 may connected to the plunger in any suitable manner such as in the process of molding the plunger 30, or the insertion needle 12 may be press-fit in the plunger 30. The recess in the plunger head 32 need not provide support for the infusion set 14 in the sense of providing resistance to removal of the infusion set 14. Such support may be provided solely by the frictional engagement of the insertion needle 12 with the cannula 26 or preferably with the seating membrane within the internal chamber of the infusion set 14. A rear end of the plunger 30 has a trigger-type actuator assembly 34 cooperating with the rear end of the device housing 28, and includes a stem, which is longitudinally split to define a pair of trigger arms 38 which have outturned trigger fingers 58 on the sides thereof. The trigger actuator assembly 34 is adapted to hold the plunger 30 in a retracted position, against the force of a compressed helical drive spring 36. The trigger arms 38 of the actuator assembly 34 are adapted for fingertip depression to release the plunger 30 for spring-loaded travel toward the advanced position, and for corresponding transcutaneous placement of the insertion needle 12, and of the cannula 26 travelling therewith, through the patient's skin. In an alterative embodiment, release of the plunger 30 may be caused by pressing manually on diametrically opposed outside areas of the device housing 28 to deform the housing 28 and thereby effect release of the trigger arms 38.

Figure 3:
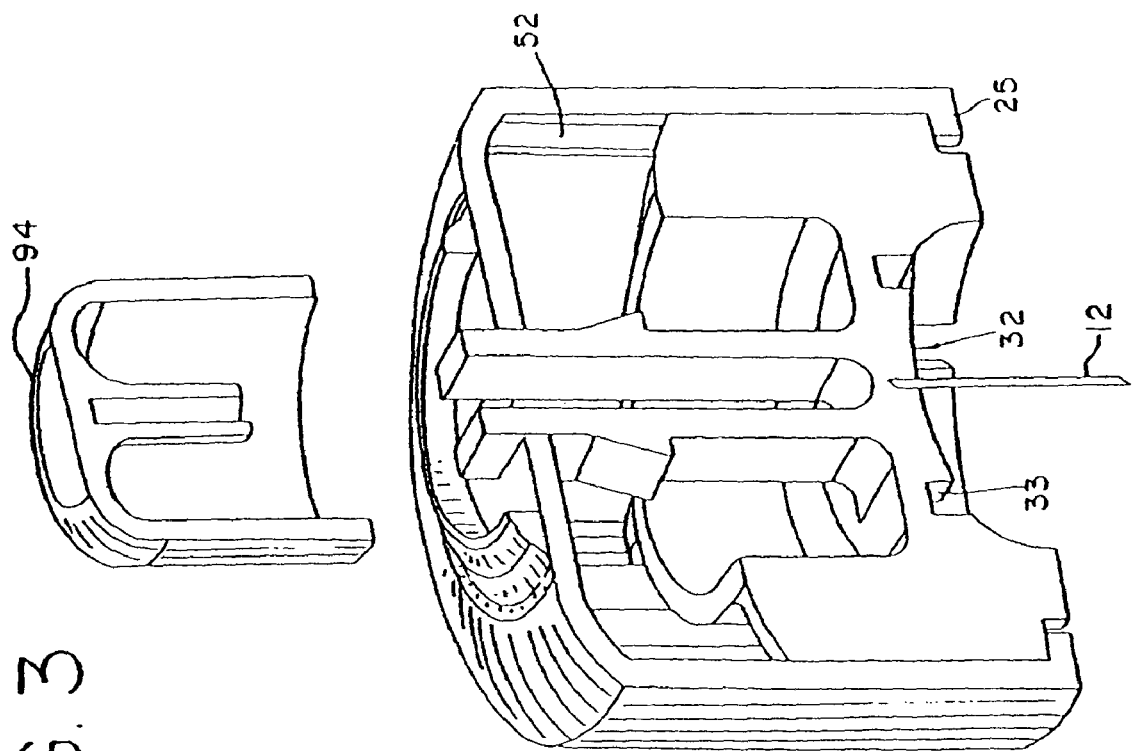
FIG. 3 is a schematic cross-sectional view of the injector device of FIG. 1, with the plunger in the advanced position and after placement of the subcutaneous infusion set.
Figure 5:
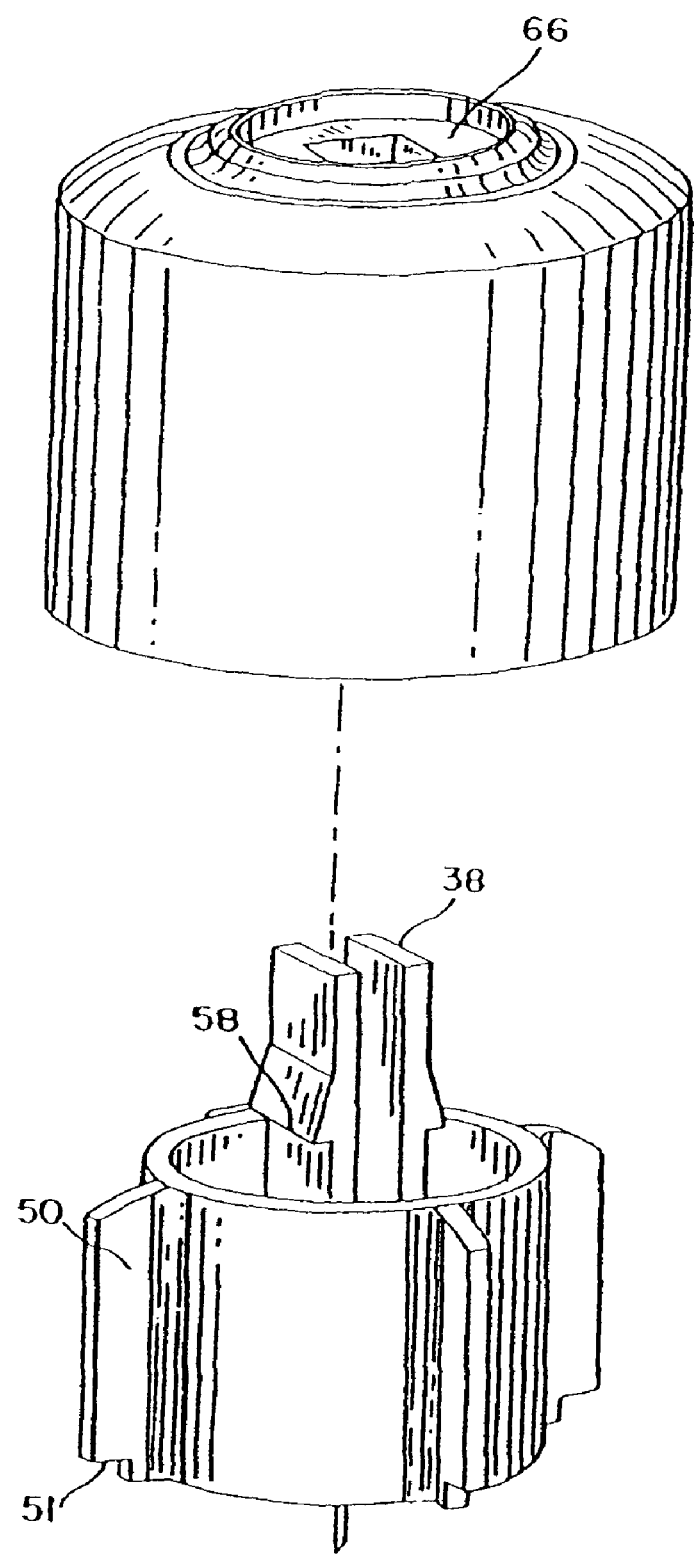
FIG. 5 is an exploded perspective view illustrating the plunger and housing parts of the injector device.
Figure 6:
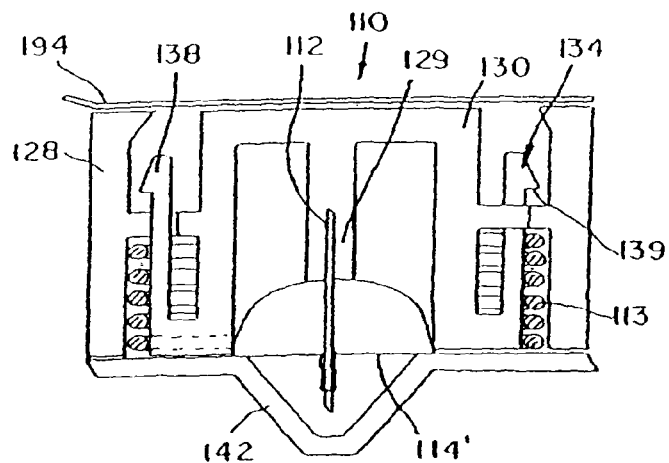
FIG. 6 is a highly schematic vertical partly cross-sectional view illustrating an injector device according to a second embodiment of the invention, prior to use.

FIGS. 1-5 illustrate construction details of the injector device housing 28, wherein the lower or nose end thereof defines a flat and generally planar peripheral surface 25 for placement against the skin of a patient with a longitudinal axis of the device housing 28 oriented generally perpendicular to the patient's skin A hollow bore of the device housing 28 has a size and shape for reception of the infusion set 14, with the insertion needle 12 extending through the cannula 26 and extending together with the cannula 26 in a direction for placement on a patient. A releasable cover sheet 42 (FIGS. 1 and 2) is preferably secured to the device housing 28 at the nose end thereof to indicate the sterility of the infusion set 14. The device housing 28 may also include a narrow slot (not shown) extending parallel with the insertion needle 12 to accommodate slide fit reception of a coupling element projecting laterally from the infusion set housing for coupling of the infusion set with a pump (not shown), and longitudinally extending track slots 52 (FIG. 3). The plunger 30 includes ribs 50 for guided reception within the track slots 52 formed in the device housing 28 to control the movement of the plunger 30 between the advanced position and the retracted position. The plunger 30 ribs 50 define a surface 51 near the head 32 adapted to cooperate with a peripheral inner edge 29 at the nose end of the device housing 28 to limit movement of the plunger, thereby defining the advanced position of the plunger 30.

Thus, the forward or nose end of the device housing 28 accommodates movement of the subcutaneous infusion set 14 between the retracted position disposed substantially at the rearward most end of the device housing 28, and the advanced position.

As will be understood, the trigger-type actuator assembly 34 generally functions to releasably retain the plunger 30 in the retracted and cocked position, ready for rapid and spring-loaded actuation upon depression of the trigger arms 38 to place the infusion set 14 on the patient. More particularly, the trigger assembly 34 is initially locked against a shoulder 66 formed on the device housing 28 by means of the trigger fingers 58. The drive spring 36 comprises a coil spring positioned about the stem on the plunger 30 and reacts between a rearward face 64 of the plunger head 32, and an internal shoulder 66' on the device housing 28. The drive spring 36 normally biases the plunger 30 toward the advanced position. During manufacture of the injector device assembly, the infusion set 14 is seated in the recess formed in the plunger head 32, either before or after the plunger 30 is moved to the retracted position. In this retracted plunger position, the drive spring 36 is retained in a compressed and cocked condition, with the cannula 26 of the infusion set 14 being received on the insertion needle 12. The releasable cover sheet 42 is then applied to the device housing 28 at the nose end thereof.

In use of the injector device 10 with the infusion set 14, the cover sheet 42 is first removed and the injector device 10 is placed firmly against the patient's skin, with the infusion set 14 supported in the proper orientation and at a predetermined distance from the skin. A cap 94, which prevents accidental projection of the infusion set 14 by preventing access to the trigger arms 38, is removed. Simple depression of the arms 38 releases the cocked plunger 30 for spring-loaded travel rapidly albeit with a controlled speed and force of insertion, to ensure penetration of the patient's skin with minimal discomfort, and in a manner which property places the insertion needle and cannula 26.

Figure 4:
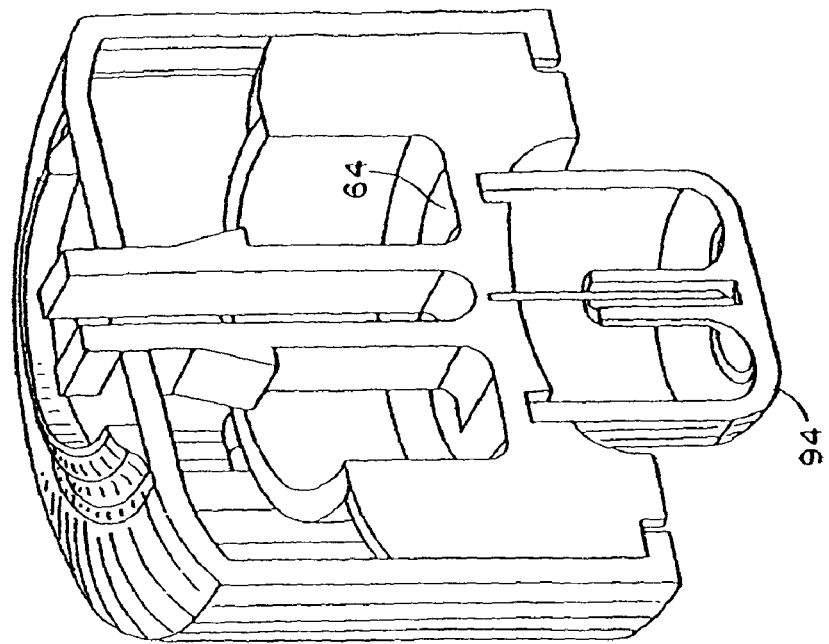
FIG. 4 is a view similar to FIG. 4 with end cap placed for protection of the protruding insertion needle.

Following placement of the infusion set 14 the injector device with insertion needle 12 is withdrawn quickly and easily from the cannula. Thereafter, the injector device can be discarded and the infusion set 14 can be used in a normal manner to deliver a selected medication through the infusion tubing and cannula 26 to the patient. As shown in FIG. 4, the safety cap 94 may conveniently be adapted to cooperate with an annular recess 33 formed in the head 32 of the plunger 30 for providing protection against the needle 12.

It is noted that the removable cap 94, when sealed to the device housing 28 at the end opposite the plunger head, together with the cover sheet 42 enable the injector device 10 together with the infusion set 14 mounted on the insertion needle 12 to be sterilised in a conventional sterilisation process using e. g. ethylene oxide, where the sterilising agent flows through the membrane formed by the cover sheet 42. By proper choice of the materials used for making the injector device, the injector device may then remain sterile under normal conditions of storage, making any external packaging unnecessary.

An alternative embodiment of the invention is shown schematically in FIGS. 6-12, wherein components corresponding in function to those described previously with respect to FIGS. 1-5 are identified by common reference numerals increased by 100. FIGS. 6-12 serve the purpose of explaining the principles involved in that embodiment, and the figures show schematic, partial cross sectional views of the injector device.

FIGS. 6-12 show an injector device assembly including a modified injector device 110 constructed from a reduced number of parts and having an alterative drive mechanism for advancing the plunger. The modified injector device 110 comprises a generally cylindrical hollow device housing 128, a plunger 130 and a trigger-type actuator 134 formed integrally with the plunger 130. A cover 194, preferably a flexible membrane, covers the top of the injector device 110 and a further cover 142 covers the bottom end of the injector device 110.

The plunger 130 has a generally cylindrical form with a head 132 and a central pin 129 including a metal insertion needle 112 secured thereto in a molding process, by press-fit, or by any other method providing a suitable resistance to toss of the insertion needle during use of the device. The pin 129 stops at a distance from a pair of outwardly turned legs 138' at the head 132, to accommodate for the infusion set 114 in the head 132 of the plunger 130. The insertion needle 112 extends through the infusion set 114 in a similar manner as described with reference to FIGS. 1-6. An infusion set tubing 113 having a typical length of between about 50 cm and 120 cm and connected to the infusion set 114 is wound up in the lower part of an annular space 115 between the device housing 128 and the plunger 130 to form part of the assembly.

Figure 9:
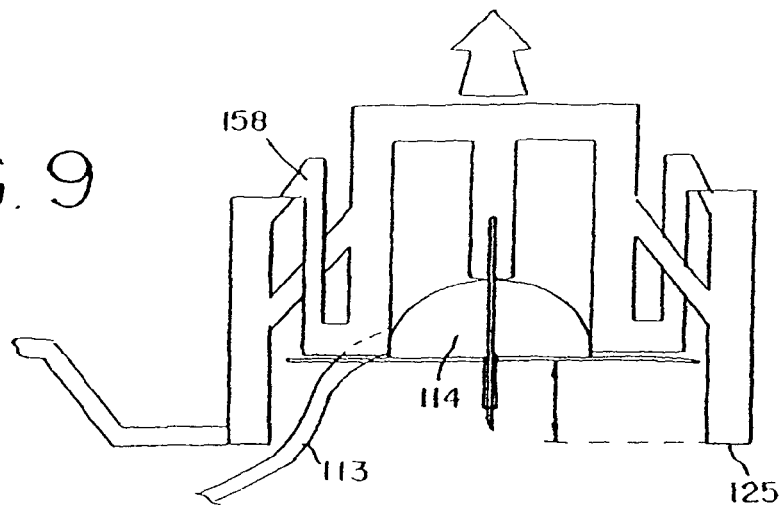
FIG. 9 is a view similar to FIG. 6 with the plunger being retracted and the injector device made ready for transcutaneous placement of the infusion set.
Figure 10:
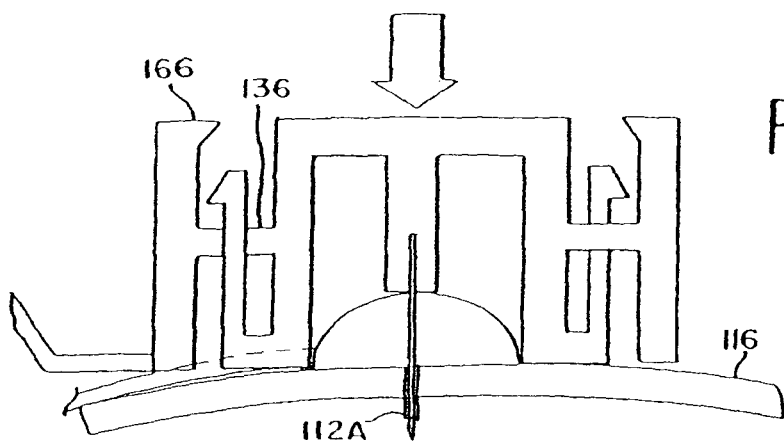
FIG. 10 is a view similar to FIG. 6, with the infusion set being placed on a patient.

More specifically, the device housing 128 again has a forward or nose end defining a flat and generally planar surface 125 for firm placement against the skin of a patient. The plunger 130 additionally includes a pair of resilient trigger arms 138 which are connected with the pair of outwardly turned legs 138' and which have out turned trigger fingers 158 at the sides thereof. The trigger arms 138 are adapted and sized for partial radial compression toward each other as they ride within the device housing when the plunger 130 is displaced from the advanced position (FIG. 6) to the retracted position (FIG. 9). As the retracted position is reached, the trigger arms 138 are spring loaded by the resiliency to move first inwardly and then outwardly whereby the trigger fingers engage the upper surface of a shoulder 166 of the device housing 128. In this position the trigger fingers 158 retain the plunger 130 in the retracted position.

A drive spring 136 is mounted within the device housing 128 to drive the plunger towards the nose of the device housing in the retracted position of the plunger 130, upon release of the trigger arms 138. The drive spring 136 is formed integrally with the device housing 128 and the plunger 130 in a molding process and may conveniently be formed of the same plastics material as the plunger 130 and the device housing 128. The spring is shown in closer details in FIG. 12. The spring 136 essentially comprises a number of elongated plastics strips 136, each extending around a respective part of the periphery of the plunger 130, in the annular space 115 between the plunger 130 and the device housing 128. The drawing show an embodiment incorporating two such strips that each extends around about one fourth of the periphery of the plunger 130. Each strip 136 is integrally connected at one end 136'' with the plunger 130 and with the device housing 128 at the other end 136'. In the advanced position of the plunger shown in FIGS. 6-8 and 10-12, the strips 136 are preferably essentially plane and non-deformed. However, when moving the plunger 130 to the retracted position shown in FIG. 9, the strips 136 of the spring are bend, setting up the required force that seeks to drive the plunger 130 towards the nose of the device housing 128. It is noted that this process normally gives rise to a rotational movement of the plunger 130 about its central axis, which is coincident with the insertion needle 112.

Figure 7:
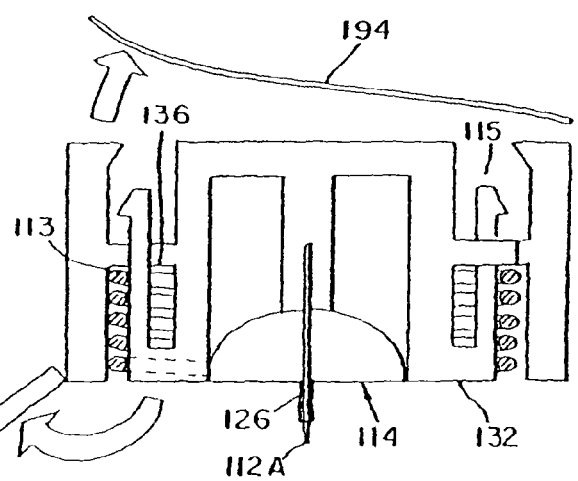
FIG. 7 is a view similar to FIG. 6. illustrating the injector device being made ready for use.
Figure 8:
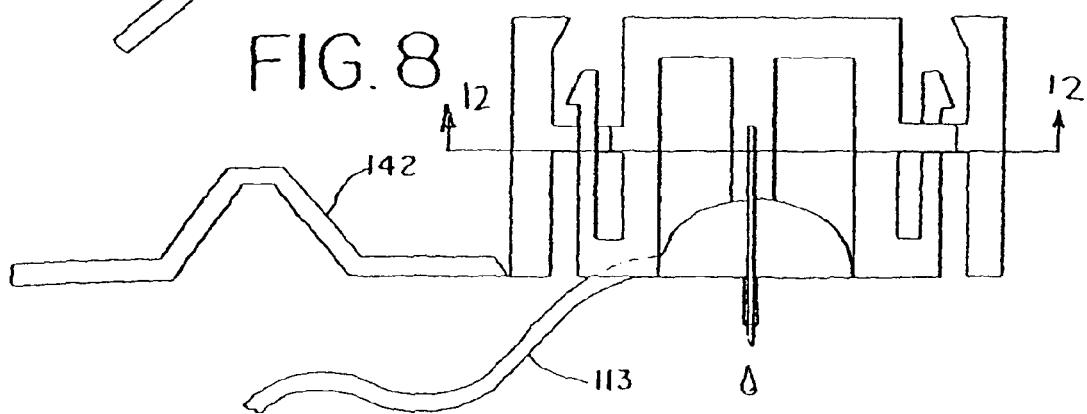
FIG. 8 is a is a view similar to FIG. 6 of the infusion set being primed.

Operation of the injector device assembly shown in FIGS. 6-12 is as follows. Since the injector device is preferably delivered to the patient in an uncocked state to simplify the process of manufacture, the plunger 130 must first be moved to the retracted position. To allow for retraction of the plunger 130, the upper cover 194, which spans across the device housing 128, and the tower cover 142 are first removed, as shown in FIG. 7. The lower cover 142 may be hingedly connected to the device housing 128. In this process, the infusion set 114 is exposed with the pointed end 112A of the insertion needle 112 projecting from the end of the soft flexible cannula 126. The infusion set tubing 113 is then connected to a suitable pump, and the infusion set 114 is primed (drop marked 300 in FIG. 8) by allowing medication to exit through the narrow annular space between the cannula 126 and the insertion needle 112 or, if a hollow needle is used, through the needle, as shown in FIG. 18 The injector device 110 is then cocked by displacing the plunger 130 with respect to the device housing 128 as illustrated by the arrow in FIG. 9, until the fingers 158 engage the upper shoulder 166 of the device housing 120, indicating that the injector device is now ready for use. A release sheet 114' is then removed exposing an adhesive material on the bottom side of the infusion housing 114, and the patient or the nursing personnel then places the injector device on the patient's skin. The plunger 130 is released by application of an inwardly directed manual force on the arms 138 to transcutaneously place the insertion needle 112 and the cannula 126. In an alternative embodiment, release of the plunger 130 may be caused by pressing manually on diametrically opposed outside areas of the device housing 128 to deform the housing 128 and thereby effect release of the trigger arms 138.

Figure 11:
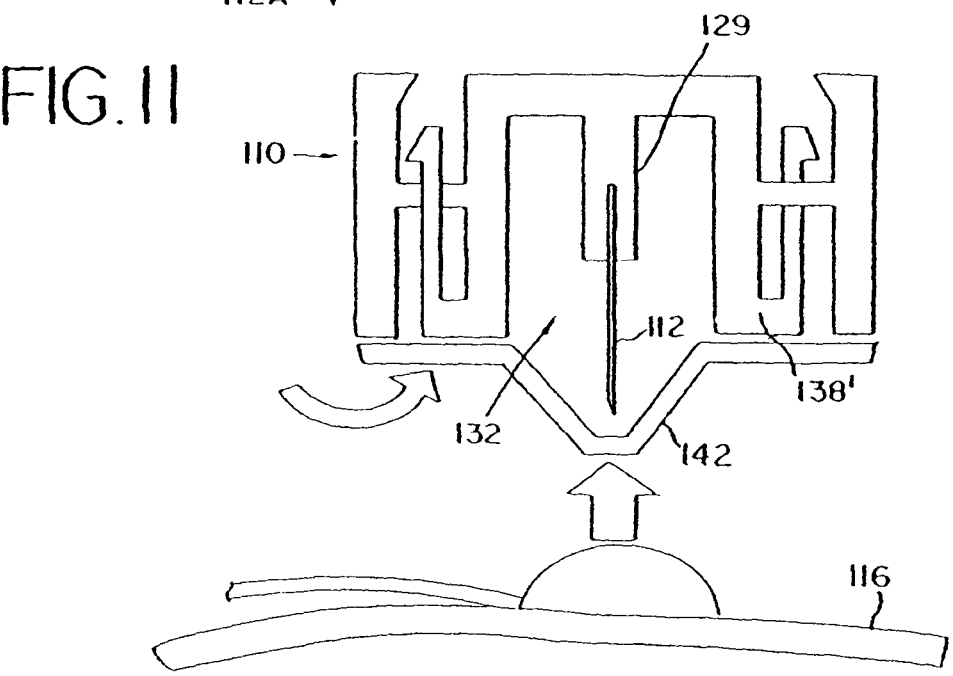
FIG. 11 is a view similar to FIG. 6, with the injection device being removed from the infusion set placed on the patient.
Figure 12:
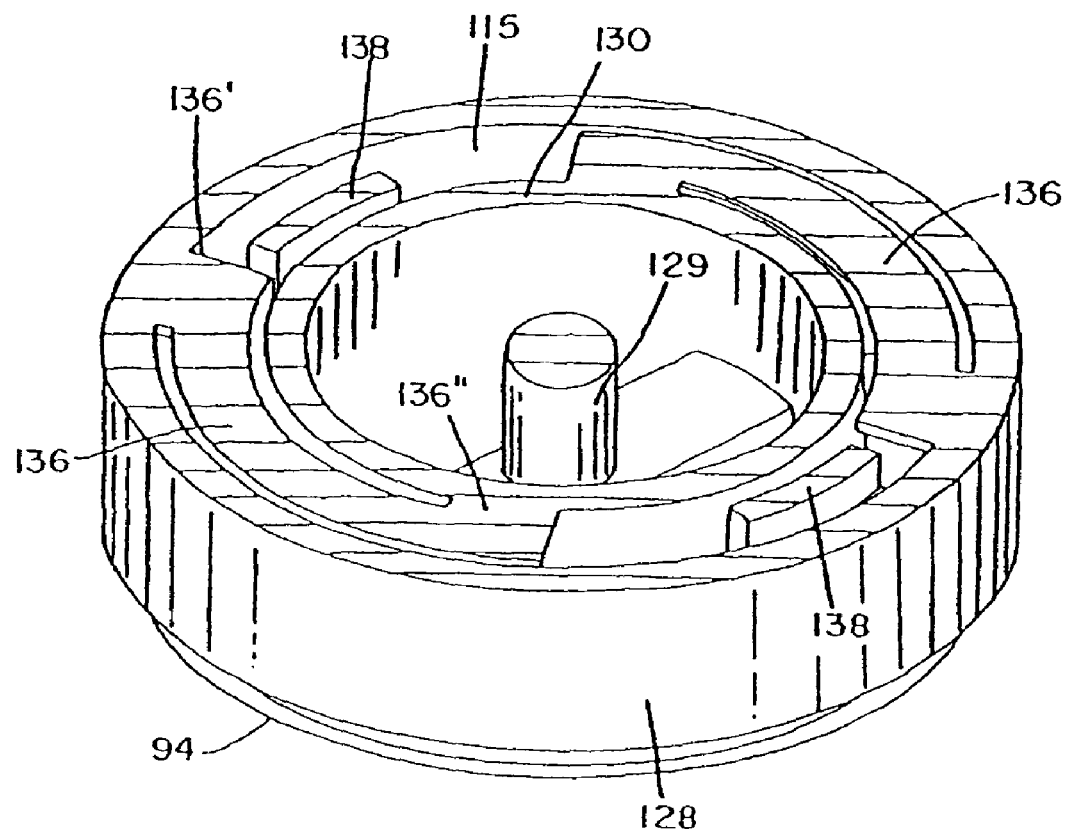
FIG. 12 is a horizontal perspective, cross-sectional view of the device shown in FIGS. 6-11, showing the spring-type drive with the plunger in the advanced position, as seen along line 12-12 in FIG. 8.

The injector device 110 is then removed, leaving the infusion set 114 on the patient's skin, illustrated by reference numeral 116, and the bottom cover 142 is then repositioned at the original place shown in FIG. 11 for protection of the insertion needle 112 which projects partially from the nose end of the device housing 128.

The removable upper cover 194 and the bottom cover 142, when sealed to the device housing 128, allow the injector device 110 together with the infusion set 14 mounted on the insertion needle 112 to be sterilised in a conventional sterilisation process using e.g. ethylene oxide. For this purpose one or both covers 142, 194 may comprise a permeable membrane allowing through flow of the sterilising agent. By choosing suitable materials, the injector device may then remain sterile for a long time under normal conditions of storage whereby no further packaging is required to ensure sterility of the assembly at the time of use For this purpose, at least one of the covers; preferably the upper cover 194, may carry printed indicia relating to the shelf life of the assembly. One suitable material for the permeable membrane is Tyvec™.

FIGS. 13-16 show a third embodiment of the invention wherein components corresponding in function to those described previously with respect to FIGS. 1-5 are identified by common reference numerals increased by 200. FIGS. 13-16 serve the purpose of explaining the principles involved in that embodiment, and the figures show schematic, partial cross-sectional views of an injector device 210. The injector device 210 is particularly suitable for the placement of a subcutaneous infusion set 214 at an acute angle relative to the skin of a patient.

Figure 13:
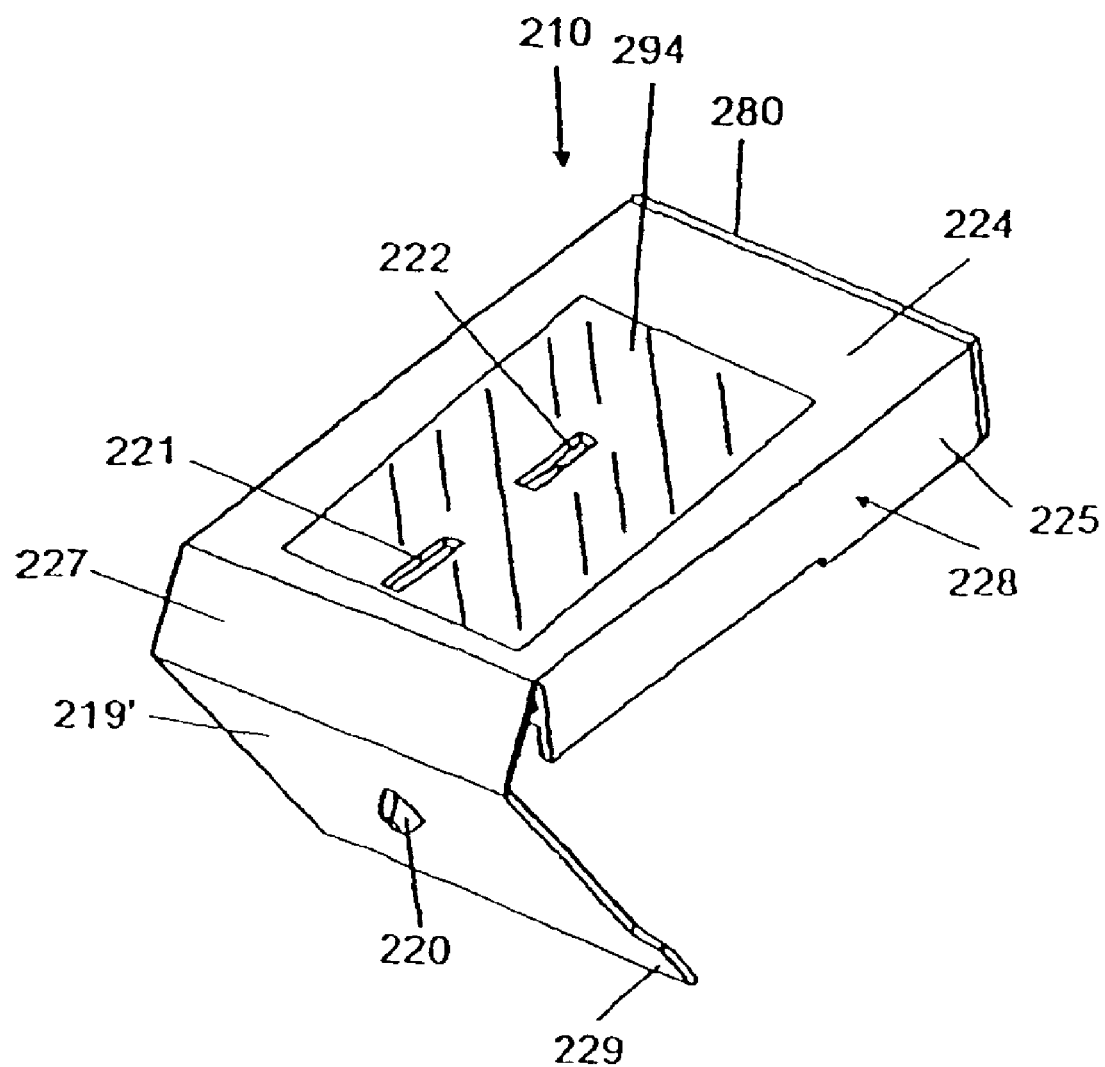
FIG. 13 is a perspective view illustrating an injector device according to a third embodiment of the invention, prior to use.
Figure 16:
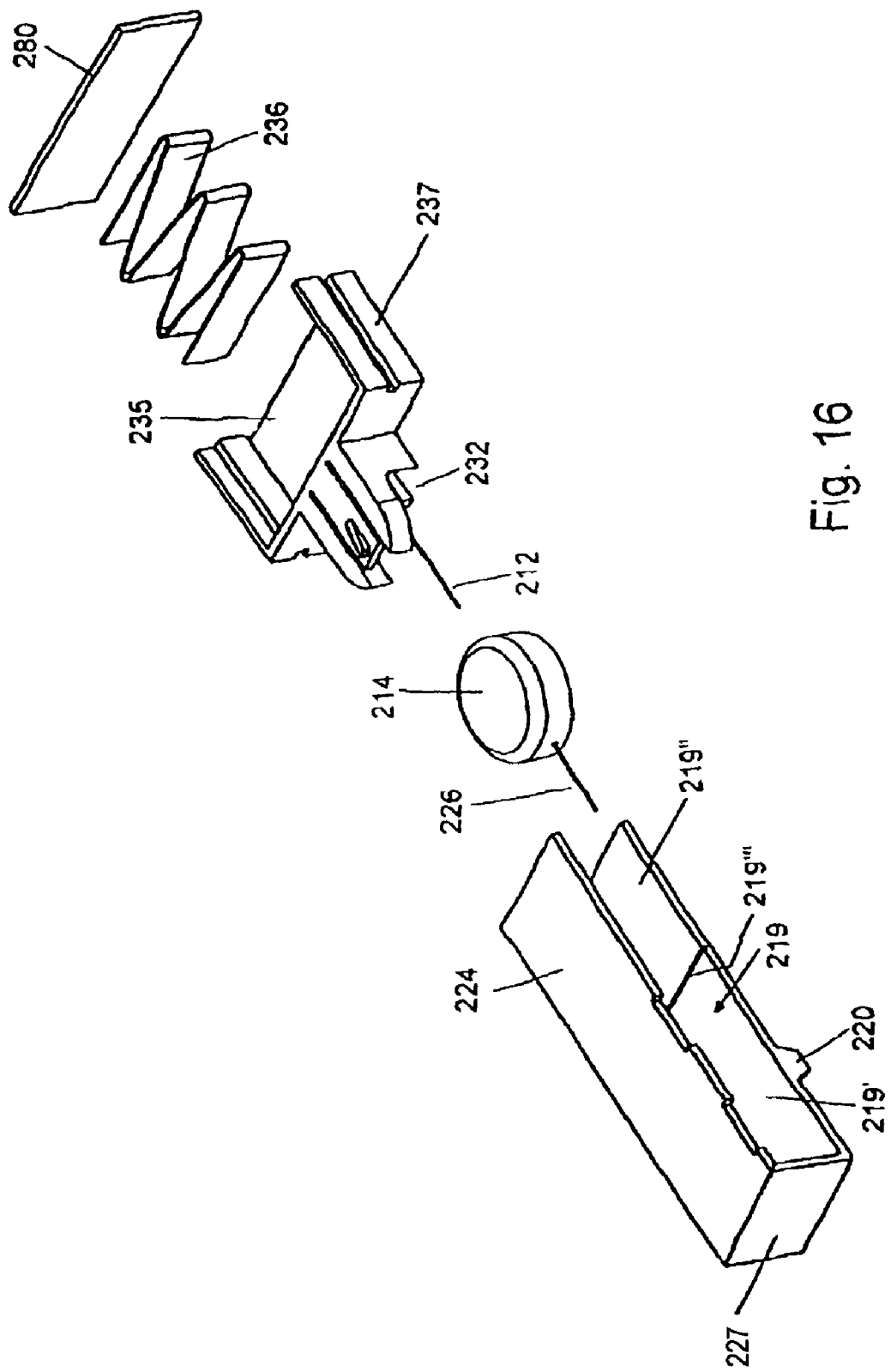
FIG. 16 is a exploded perspective view illustrating the various parts of the injector device of FIGS. 13-15.

As best seen in FIG. 13, which shows the injector device in a semi-open state, the injector device 210 has a device housing 228 with a flattened box like structure with parallel major walls 224, 219, the wall 219 including a frangible area 219'''', see FIG. 16, allowing the wall 219 to be split by manually pulling flap 229 (FIG. 13), thereby forming two separate wall parts 219', 219'' for a purpose that will be explained later. The housing 228 also includes a front wall 227 at the nose end of the injector device, and a rear wall 280, and opposed parallel side walls 225 frangibly connected to wall part 219'. The injector device 210 is presented to the consumer as a closed, box shaped item, which may easily be provided with printed text as required.

Figure 14:
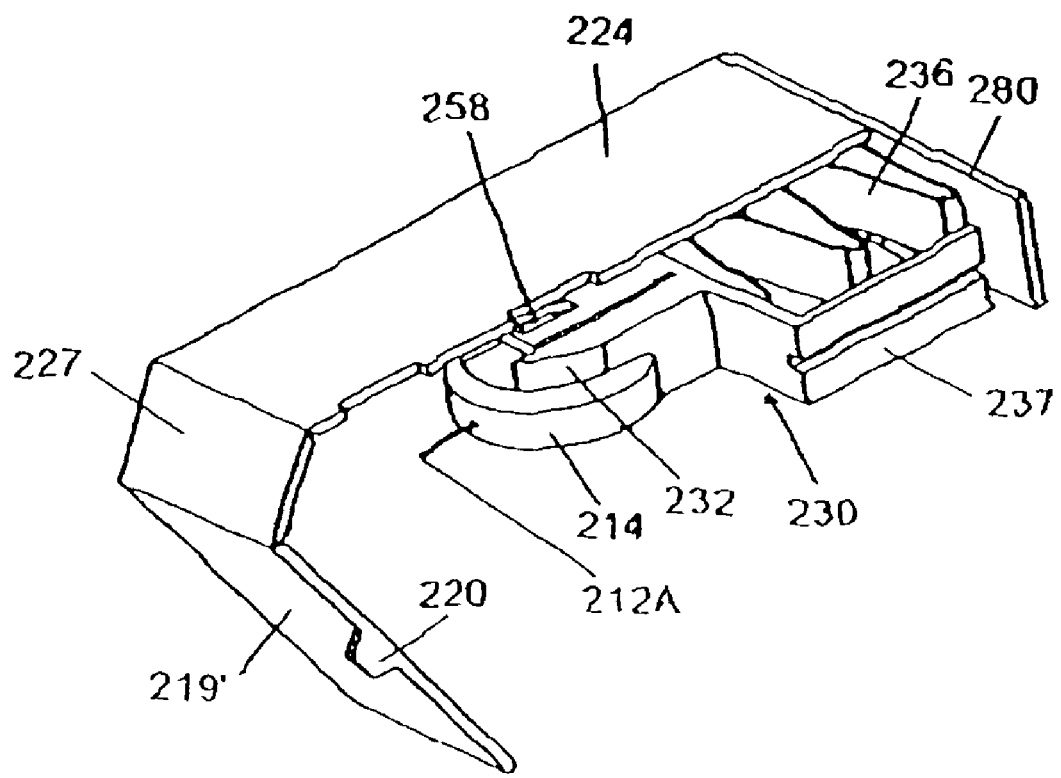
FIG. 14 is a perspective, partly cross-sectional view of the device of FIG. 13.

FIG. 14 shows the injector device in the same state shown in FIG. 13; however, a part of the walls 224, 227 and 219, as well as wall 225 have been omitted to show the interior of the injector device 210.

Figure 15:
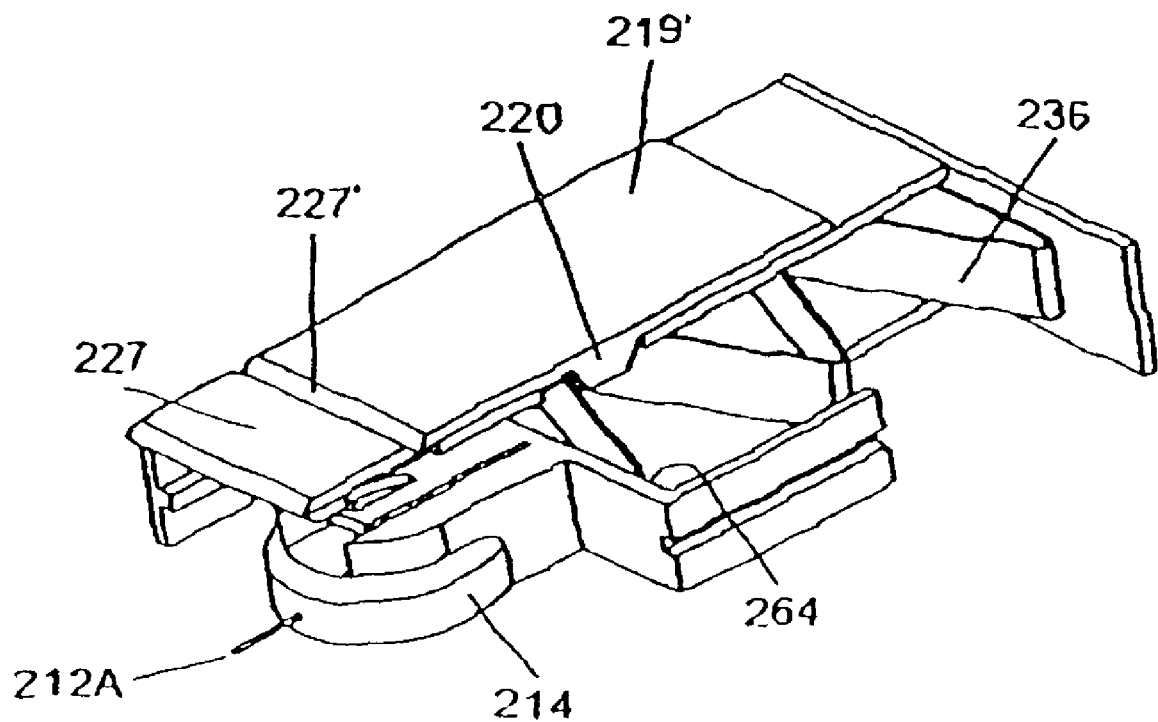
FIG. 15 is a view similar to FIG. 14, showing the plunger in the advanced position.

The injector device 210 comprises a plunger 230 mounted for longitudinal sliding movement within the box shaped housing between a rearward retracted position (FIG. 14) and a forward advanced position (FIG. 15). The device housing 228 and the plunger 230 are preferably formed of a plastics material. The device housing 228 may alternatively be manufactured from a blank of rigid cardboard. The plunger 230 has a recessed head 232 (best seen in FIG. 16) at a forward end thereof shaped for receiving the housing of a subcutaneous infusion set 214. Centrally in the recess, the head 232 is provided with a projecting metal insertion needle 212 securely connected thereto. The plunger 230 need not provide support for the infusion set as understood in the sense of providing resistance to removal of the infusion set. Such support may preferably be provided by the frictional engagement of the insertion needle 212 with the infusion set 214. A drive spring 236 positioned behind wall 280 reacts between a rearward faces 264 of the plunger head 232. The drive spring 236 normally biases the plunger 230 toward the advanced position. The front end of the plunger 230 has a trigger button 258 cooperating with the wall 224 of the device housing 28. In the retracted state of the plunger shown in FIG. 14, the trigger button 258 extends through an opening 222 formed in the upper wall 224 of the device housing 228 and aligned for reception of a release tab 220 on the wall 219', as will be explained.

The trigger button 258 may be adapted for fingertip depression to release the plunger 230 for spring-loaded travel toward the advanced position, and for corresponding transcutaneous placement of the insertion needle 212, and of the cannula 226 travelling therewith, through the patient's skin. Preferably, the button 258 is depressed by pivoting wall part 219' about line 227'. When the tab 220 formed on the external surface of wall part 219' is aligned with the slot 220, the trigger button 258 can be depressed to actuate the spring-locked plunger, by manually pressing down wall part 219'.

Before opening the device housing 210, that is; before separating wall 219, 219' along frangible line 219''', the assembly is maintained under sterile conditions. A removable cover sheet 294 (FIG. 13) is sealed to wall 224 to cover opening 222. All other walls defining the closed housing 210 being sealed together, the cover sheet 294, when being permeable allows the injector device 210 together with the infusion set 214 mounted on the insertion needle 212 to be sterilised in a conventional sterilisation process using e.g. ethylene oxide, where the sterilising agent flows through the permeable membrane.

Figure 17:
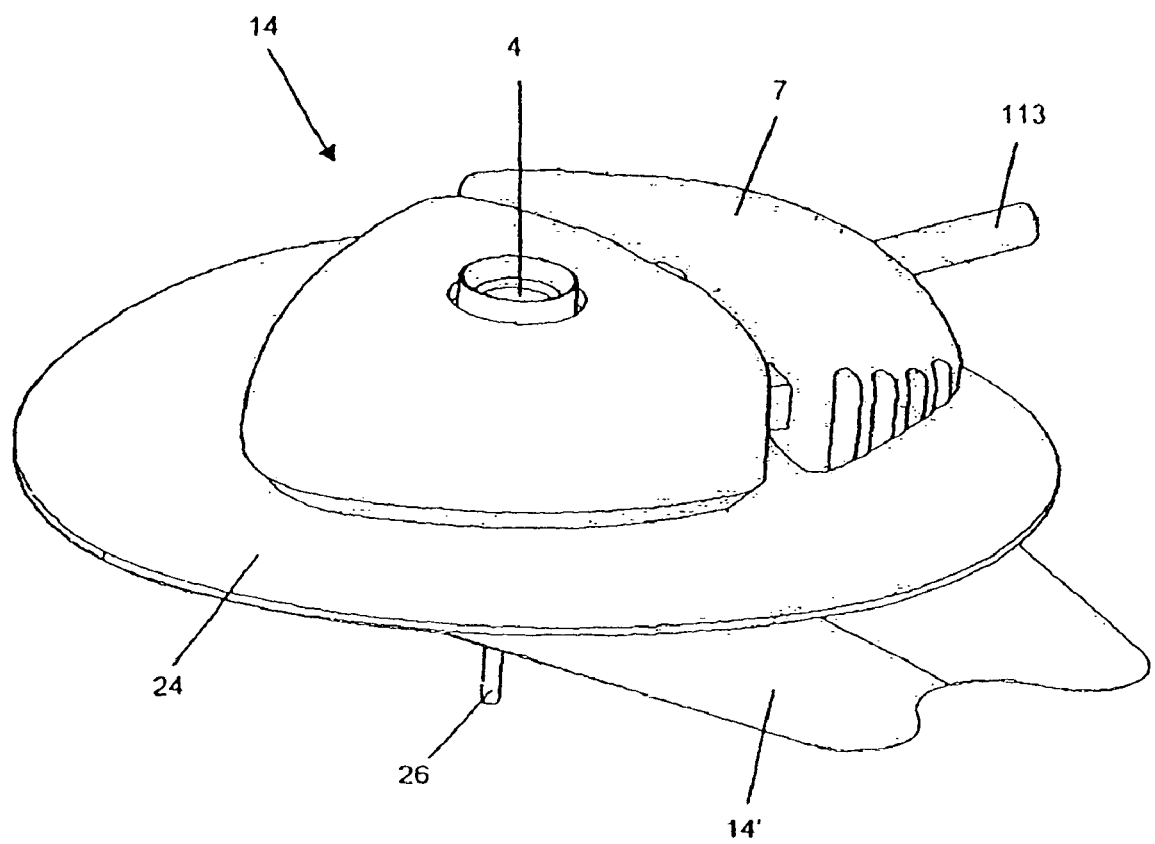
FIG. 17 is a perspective view of an infusion set suitable for use with the injector device of the invention.

FIG. 17 shows an example of an infusion set 14 suitable for use with the injector device according to the invention. The infusion set 14 includes a housing 3 with an internal chamber (not shown). The internal chamber receives medication via infusion tubing 113 which may be detachably connected to the housing 3 by any suitable connector 7. The base 24 of the housing 3 maybe a flexible sheet of a woven material secured to the housing 3 such as by means of an adhesive and carrying an adhesive covered by a release sheet 14' which is removed to expose the adhesive prior to placement of the infusion set. The infusion set 14 has a protruding soft and flexible cannula 26, which communicates with the internal chamber. An internal passage which is sealed by a sealing membrane 4 and which is penetrated, by the insertion needle of the injector device extends through the housing opposite the cannula 26.

FIG. 18 shows how priming of the infusion set may be carried out prior to the placement of the infusion set using an injector device with a plunger shown only in part and carrying a hollow insertion needle 12, 112 having a lateral opening 12B, 112B. The medical insertion needle 12, 112 of the injector device extends into the internal chamber 2 of the infusion set 14 and through the cannula 26, 126, when the infusion set 14 is mounted in position on the injector device. Medication 6 is then supplied through tubing 113, into the internal chamber 2. To allow the user to visibly confirm that the internal chamber 2 has been completely filled with medication, the lateral opening 12B, 112B allows the medication to flow into the interior of the needle 12, 112 and to exit through pointed end 12A, 112A.

Figure 19:
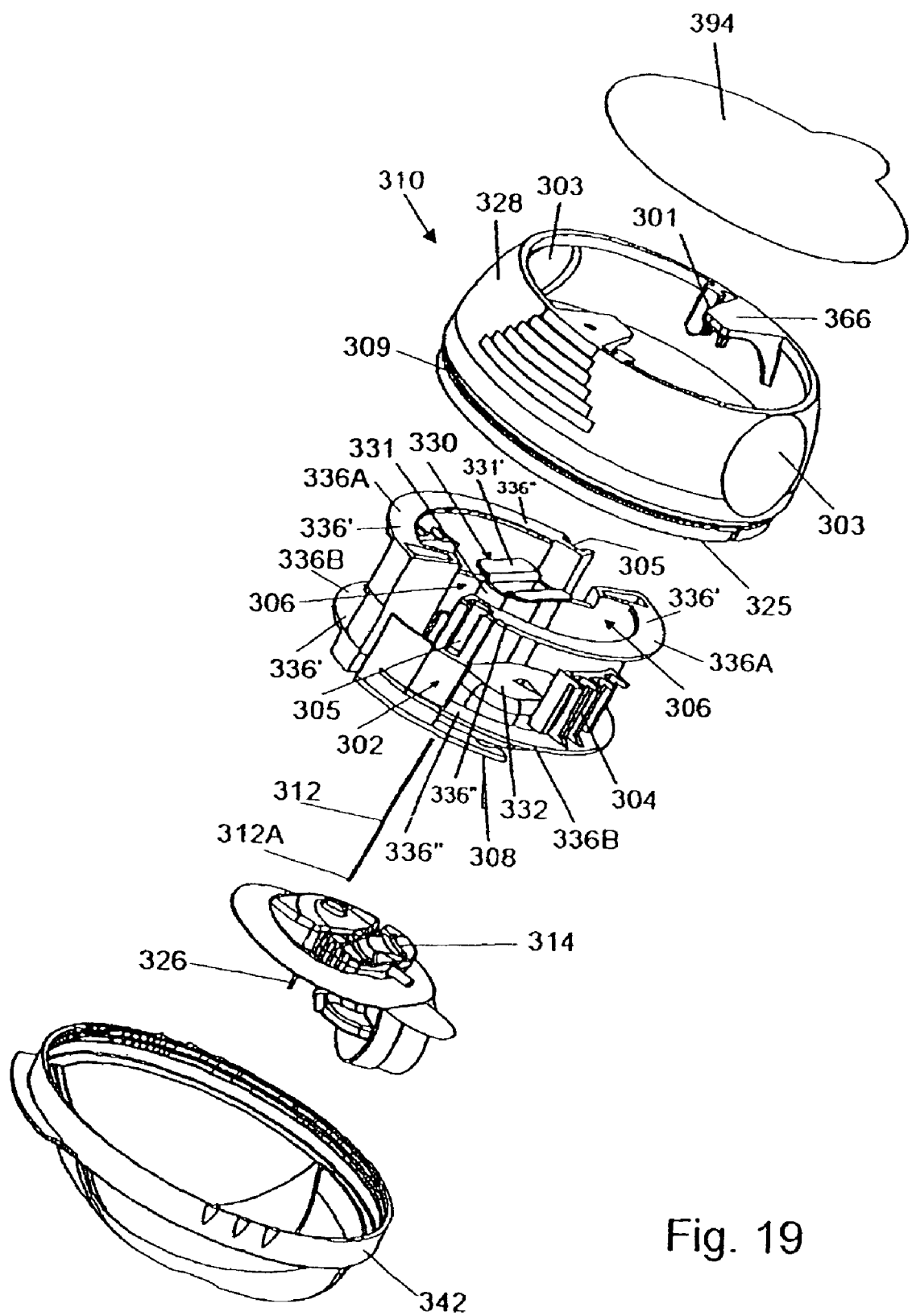
FIG. 19 shows in an exploded view a presently preferred embodiment of the injector device assembly, similar to the embodiment of FIGS. 6-12, wherein the plunger has an insertion needle secured thereto.

FIG. 19 shows in an exploded view a presently preferred embodiment of the injector device assembly. In respect to FIGS. 6-12, elements having a similar function are identified by the same numerals increased by 200.

The injector device 310 includes respective removable covers 342, 394, the cover 342 having a hollow for accommodating a part of the insertion needle 312 when the cover 342 is secured to the housing 328, such as by snap engagement with the rim 309 of the housing 328. The cover 342, the housing 328, the plunger 330 and a drive with a spring for advancing the plunger 330 to the advanced position are preferably made of plastics while the cover 394 may be a flexible foil secured to the housing 328 by an adhesive. Preferably, the coves 342, 394 serve as bacterial barriers, the flexible foil 394 being of medical paper. An insertion needle 312 is preferably secured in a stable manner to the plunger 330 of the injection device, such as by press-fitting, the plunger 330 having a narrow central passage wherein an end of the insertion needle 112 is lodged. As will appear, the plunger 330 and the drive may conveniently be formed integrally as a single component in a moulding process.

The ring-shaped housing 328 is flexible in the sense that the application of a manual force against diametrically opposed depressions 303 of fingertip size will give rise to a slight deformation of the housing 328 such that it assumes a slightly oval shape when viewed from above for bringing about a release of the plunger in the retracted position and cause a spring loaded movement of the plunger 330 towards the advanced position, as will be explained For maintaining the plunger 330 in the retracted position the housing 328 is provided with two opposed ledges 366. Moreover, the housing 328 is provided with opposed dovetail projections 301 extending along the same general direction as the insertion needle 312 and adapted to connect with complementary recesses in the aforementioned spring, to secure the spring in relation to the housing 328.

Figure 20E:
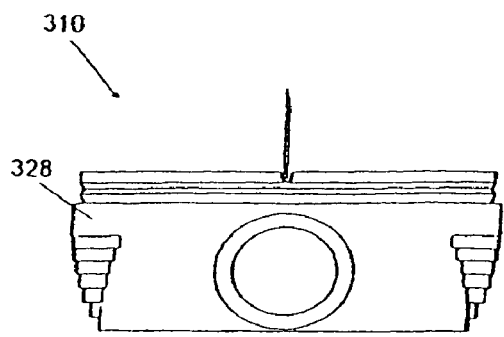
Figure 20C:
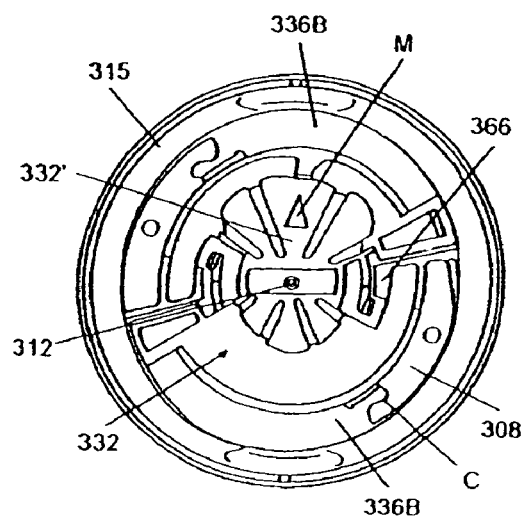
FIGS. 20c and 20d show bottom and top views of the injector device shown in FIGS. 20a and 20b.
Figure 20D:
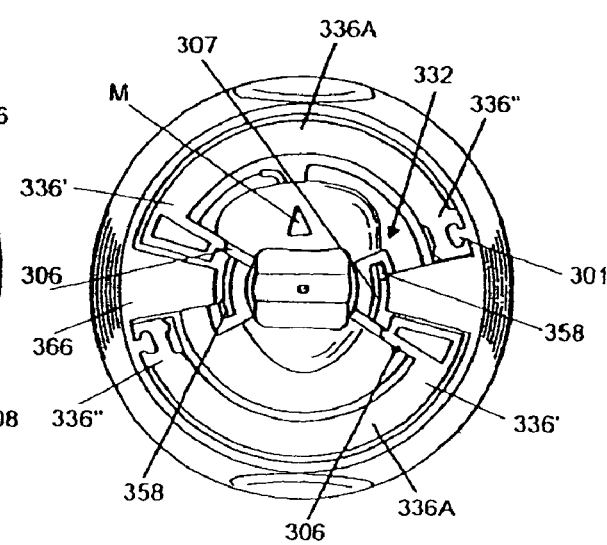
Figure 20A:
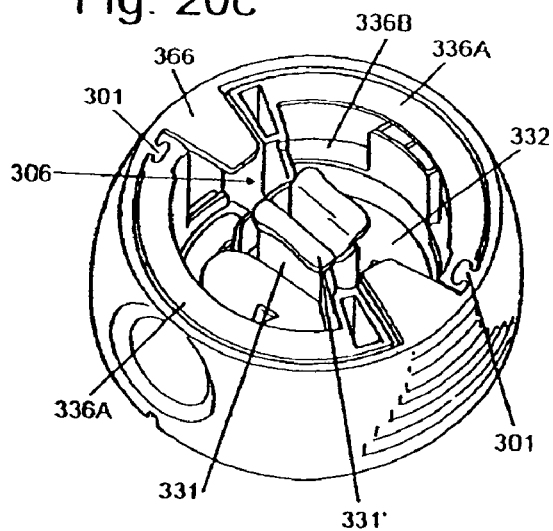
FIGS. 20a and 20b show a perspective view of the injector device of FIG. 19 with the plunger in the advanced position.
Figure 20B:
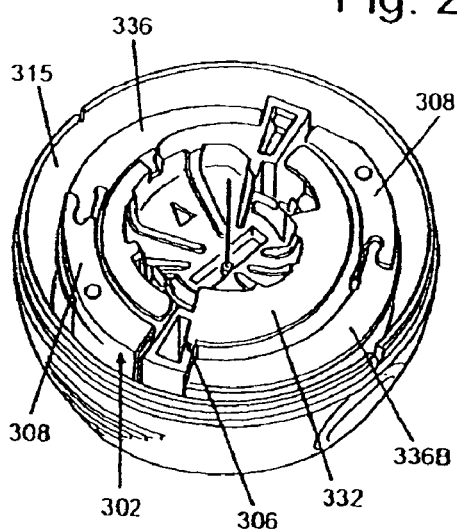
Figure 21A:
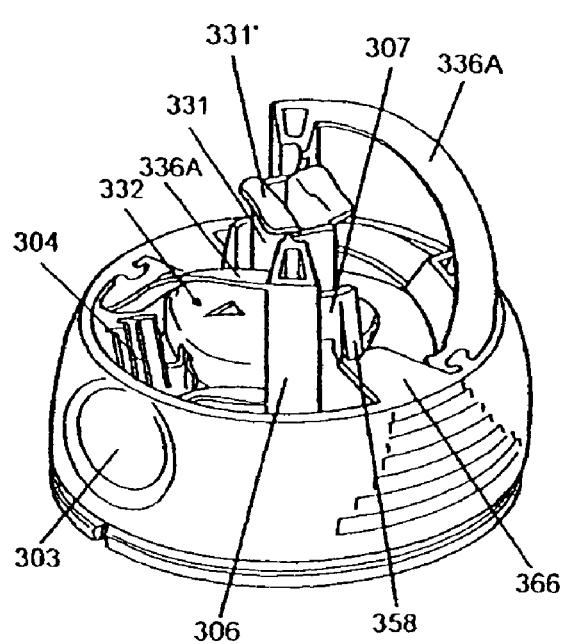
FIGS. 21a and 21b show in a perspective view the injector device of FIG. 19 with the plunger in the retracted position.
Figure 21B:
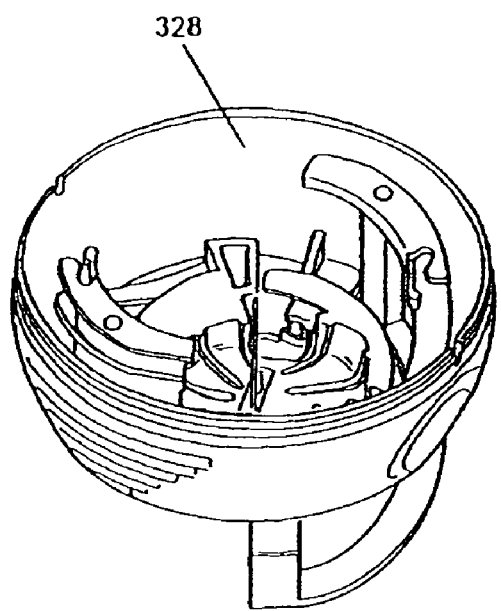
Figure 21C:
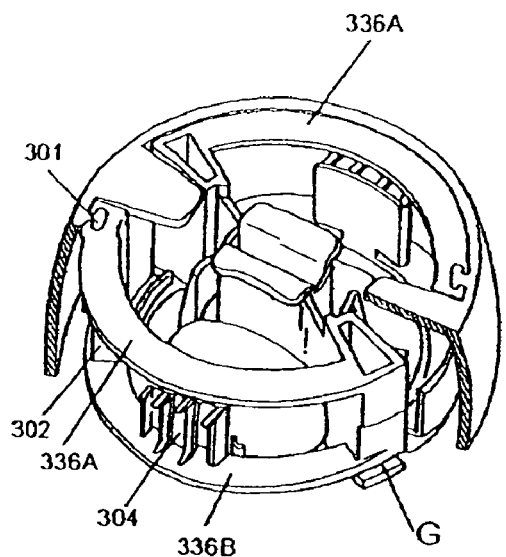
FIGS. 21c-e are views similar to FIGS. 20a, 21a and 21b with part of the housing being cut away.
Figure 21D:
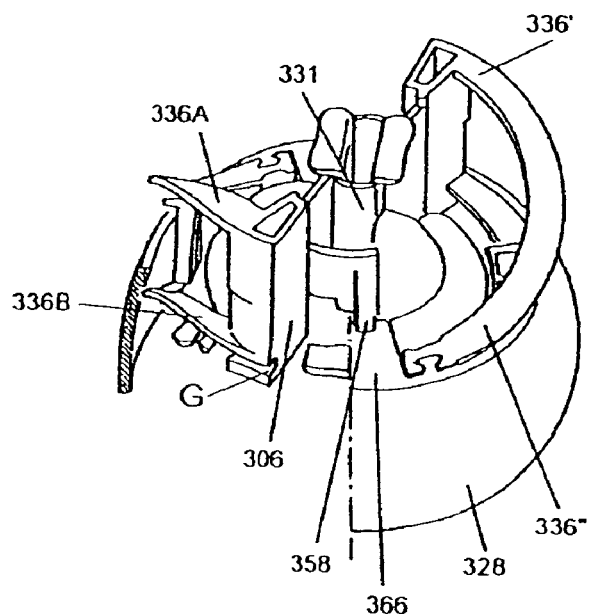
Figure 21E:
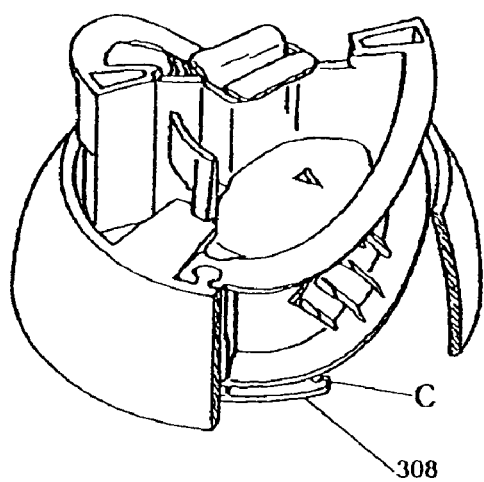

The plunger 330 generally includes a head 332, a hub 331 and, opposite the head 332, an enlarged gripping portion 331' which allows a user to manually pull the plunger 330 to a retracted position. The head 332 preferably carries a marking M representing the place where the 113 tubing exits the infusion set 314 located there under whereby the user can check the orientation of the tubing after placement of the infusion set. The head 332 moreover has a recess 332' for accommodating the infusion set 326 with cannula 326 through which the insertion needle 312 extends, the infusion set 314 preferably being maintained in position by frictional engagement of the insertion needle 312 with an inside surface of the infusion set 314. The plunger 330 has two opposed rigid walls 306 extending radially outwardly from the hub 331. The walls 306 extend in the axial direction of the device 310, i.e. in the same general direction as the insertion needle 312, and are connected to the aforementioned spring. Moreover, as best seen in FIG. 20d, the walls 306 each carry a lateral projection 307 with a finger 358 which is releasably locked in engagement with a corresponding one of the ledges 366 of the housing 328 by snap action in the retracted position of the plunger 330. The depressions 303 preferably being offset with respect to the ledges 366 by about 90° will cause the opposed ledges 366 to move apart when the aforementioned manual force is applied and the housing 328 assumes an oval shape, thereby bringing the finger 358 on each wall 306 out of engagement with, the corresponding ledge 366. For retaining a proximal part nearmost the infusion set of a tubing 113 (not shown) wound around the plunger 330 in the same general manner shown in FIG. 6, wall 306 has a groove G best seen in FIG. 21c and d sized to receive a small length of the tubing and to prevent the infusion set 314 from being inadvertently pulled away from the plunger 330 by the user when the tubing is unwound for connection with a medical fluid supply.

The drive which acts to drive the plunger 330 from the retracted position towards the advanced position when the fingers 358 are disengaged comprises a spring including four thin and flexible plastics strips, of which two opposed strips 336A extend about halfway around the plunger 330 at the level of the gripping portion 331' while two other opposed strips 336B extend about halfway around the plunger 330 at the level of the head 332, as viewed in the advanced and unbiased position of the plunger shown in FIGS. 19 and 20a-e. One end 336' of one of the strips 336A and one end 336' of one of the strips 336B is rigidly connected to one of the walls 306, while one end 336? of the other one of the strips 336A and one end 336' of the other one of the strips 3368 is rigidly connected to the other one of the walls 306. Preferably, the strips 336A and 336B are integrally connected with the walls 306 in a moulding process where the plunger 330 and the spring formed from the strips 336A and 336B is formed in one moulding operation The spring also comprises two rigid opposed rigid walls 302 that extend in the axial direction of the device 310 and that are each rigidly connected with the second end 336" of one of the strips 336A and the second end 336" of one of the other strips 336B. The rigid walls 302 are preferably integrally connected with the strips 336A and 336B at the second end thereof. The walls rigid 302 each have an axially extending recess 305 which is complementary with the dovetail projection 301 on the housing 328. When the plunger 330 with the spring is mounted within the housing 328 the dovetail projection 301 is slid into the recess 305 by axial movement; by selecting proper dimensions of the dovetail projection 301, and possibly also by performing this operation at a predetermined temperature, a press-fit may result that prevents subsequent removal of the plunger 330. Alternatively, or additionally, the plunger 330 may be secured using glue, or using a welding process. The two rigid walls 302 of the spring also comprise a respective projection 308 with a lower surface which in the advanced position of the plunger 330 is essentially coplanar with the rim 309 of the housing 328. The projections 308 include a clip-like retainer C for securing a distal part of the tubing wound around the plunger 330, thereby maintaining the tubing in position until unwound by the user.

As will be understood, the walls 302 are fixed in relation to the housing 328, and the strips 336A and 336B, being thin and flexible, define the parts of the spring that undergo a change in shape upon retraction of the plunger 330 and that through this change of shape generate the force acting on the plunger 330 via the connections at the ends 336' and required to advance the plunger 330 to the advanced position upon disengagement of the fingers 358. The shape of the strips 336A and 336B in the deformed condition when the plunger 330 is held in the retracted position is shown in FIGS. 21a-d. The connection between the strips 336A, 336B and the walls 302, 306 being rigid, in the sense that bending moments arising in the strips 336A, 336B upon retraction of the plunger 330 are transferred to the walls 302, 306, brings about a deformation of the strips 336A, 336B as shown.

It will be understood that the resiliency of the spring is generally defined by the elastic properties of the flexible strips 336A, 336B which should be selected such that the drive is capable of advancing the plunger 330 to the advanced position at least once, following retraction. The spring would normally allow the piston to be retracted several times, and provide the required force for subsequently advancing the plunger 330. However, the device being normally a disposable unit requires the spring to be formed with the capability to only a limited number of times advance the plunger 330 at one given speed, and the spring need not be capable of returning the plunger to the exact original position after several times of use.

As seen best in FIG. 19; the two strips 336B each carry a wall member 304 which provides support for a tubing (not shown) connected to the infusion set 314 and wound around the plunger 330 in the annular space 315 between the plunger 330 and the housing 328.

Figure 22A:
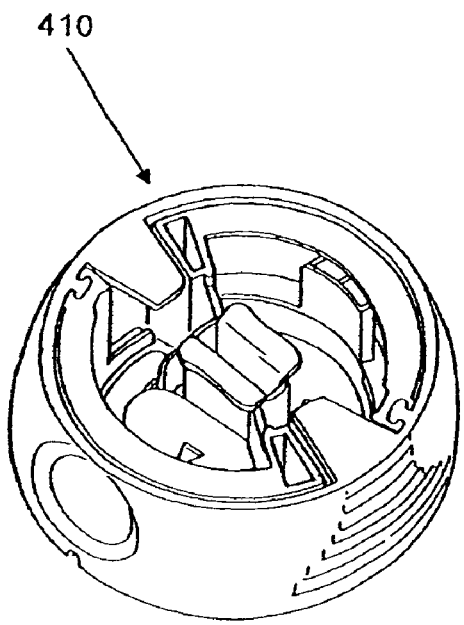
FIGS. 22a and 22b show an injector device without an insertion needle secured to the plunger.
Figure 22B:
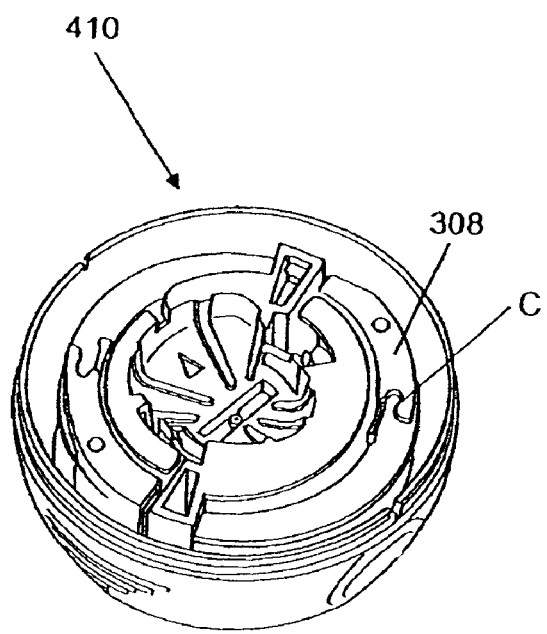

FIGS. 22a and 22b show an injector device without an insertion needle secured to the plunger.

Figure 23B:
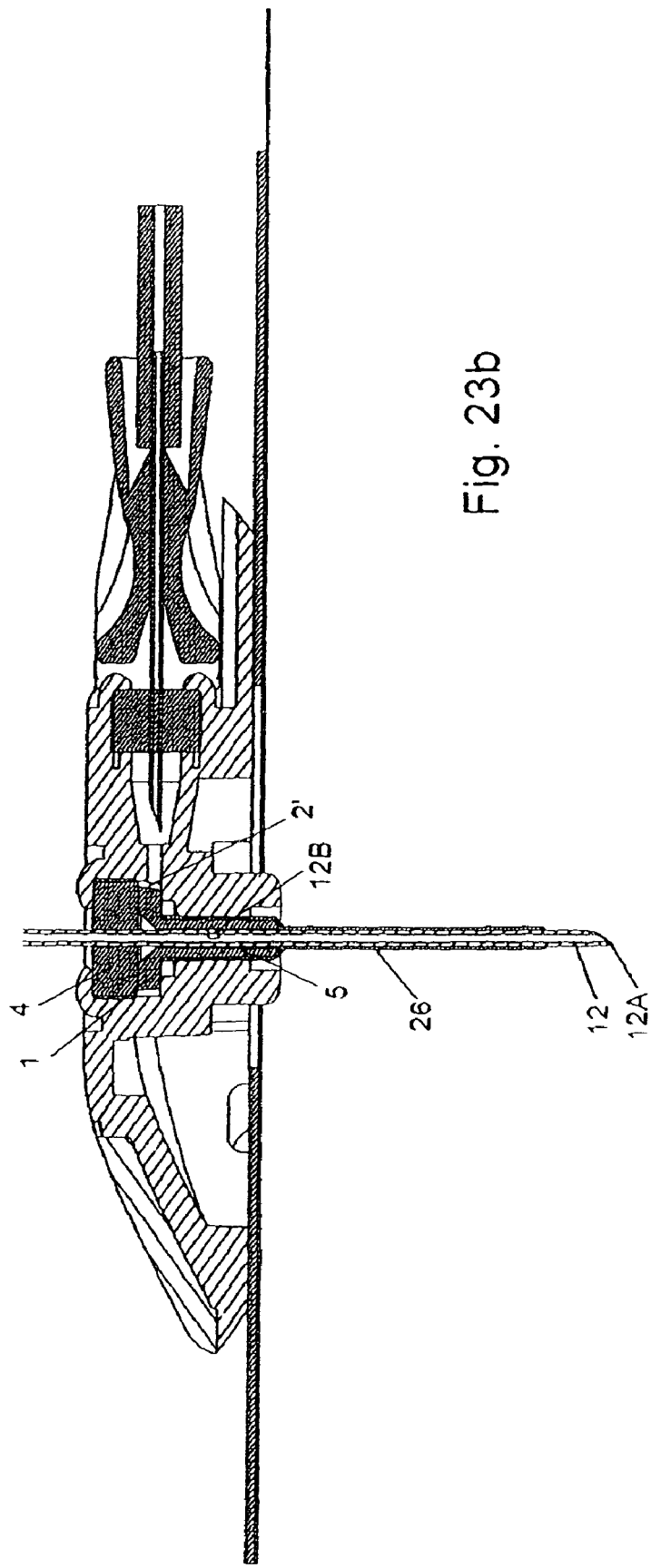

FIGS. 23a and 23b show a schematic cross sectional view through the infusion set 14 of FIG. 17. This preferred infusion set is equally suited for use with or without the injector device described herein. As shown in FIG. 23a, the plastics infusion set housing 3 has an internal chamber including a narrow cylindrical portion 2 and an enlarged cylindrical portion 2', in an upper part of which is fixed a sealing membrane 4 which may be penetrated by a retractable insertion needle 12 with a pointed end 12A, shown in FIG. 23b, for placing the infusion set 14 on a patient by means of a flexible cannula 26. The cannula 26 has a small diameter tubular portion 26" and a larger diameter tubular portion 26' which is press-fit or otherwise secured inside the narrow cylindrical portion 2 of the housing 3 chamber. A plug-like hollow tubular member 1 has a head portion nested in the enlarged cylindrical portion 2', and a portion 1" of smaller external diameter which extends into the larger diameter tubular portion 26' of the cannula, preferably applying a radial pressure against the inside surface of the cannula 26 to thereby secure the cannula in place within the narrow cylindrical portion 2 of the housing 3 chamber. For this purpose, the plug-like hollow tubular member 1 preferably exhibits some resiliency.

The head portion of member 1 has an upper surface bearing tightly against the sealing membrane 4, and has a diameter selected such that an annular passage 2" is defined between the head portion and the housing 3 wall defining the enlarged cylindrical portion 2' of the internal chamber. This annular passage is in communication with infusion tubing 113 supplying fluid to the infusion set 14. The head portion of member 1 moreover has a number of radially directed entry ports 1' of which one is shown in FIG. 23a, thereby allowing fluid to flow from the passage 2" into the interior of member 1 and further on into the small diameter tubular portion 26" of the cannula 26", and into the patient when the infusion set has been secured in place by an adhesive on base 24. The base 24 of the housing 3 may be a flexible sheet of a woven material secured to the housing 3 such as by means of an adhesive and carrying an adhesive covered by a release sheet 14' which is removed to expose the adhesive prior to placement of the infusion set FIG. 23b shows how the infusion set may be primed prior to placement, when a hollow insertion needle 12, which may be secured to a plunger of the injector device described herein, extends through the cannula 26. The hollow insertion needle 12 has a lateral opening 12B that defines an entry port whereby fluid entering the interior of member 1 through the entry ports 1' may flow into the interior of the hollow insertion needle 12 and out of the insertion needle 12 at pointed end 12A. For establishing communication, the inside diameter of the portion 1" of member 1 may as shown be slightly greater than the outside diameter of the insertion needle 12 such that an annular passage 5 is formed allowing fluid to flow from tubing 113 into the insertion needle 12.

Figure 24:
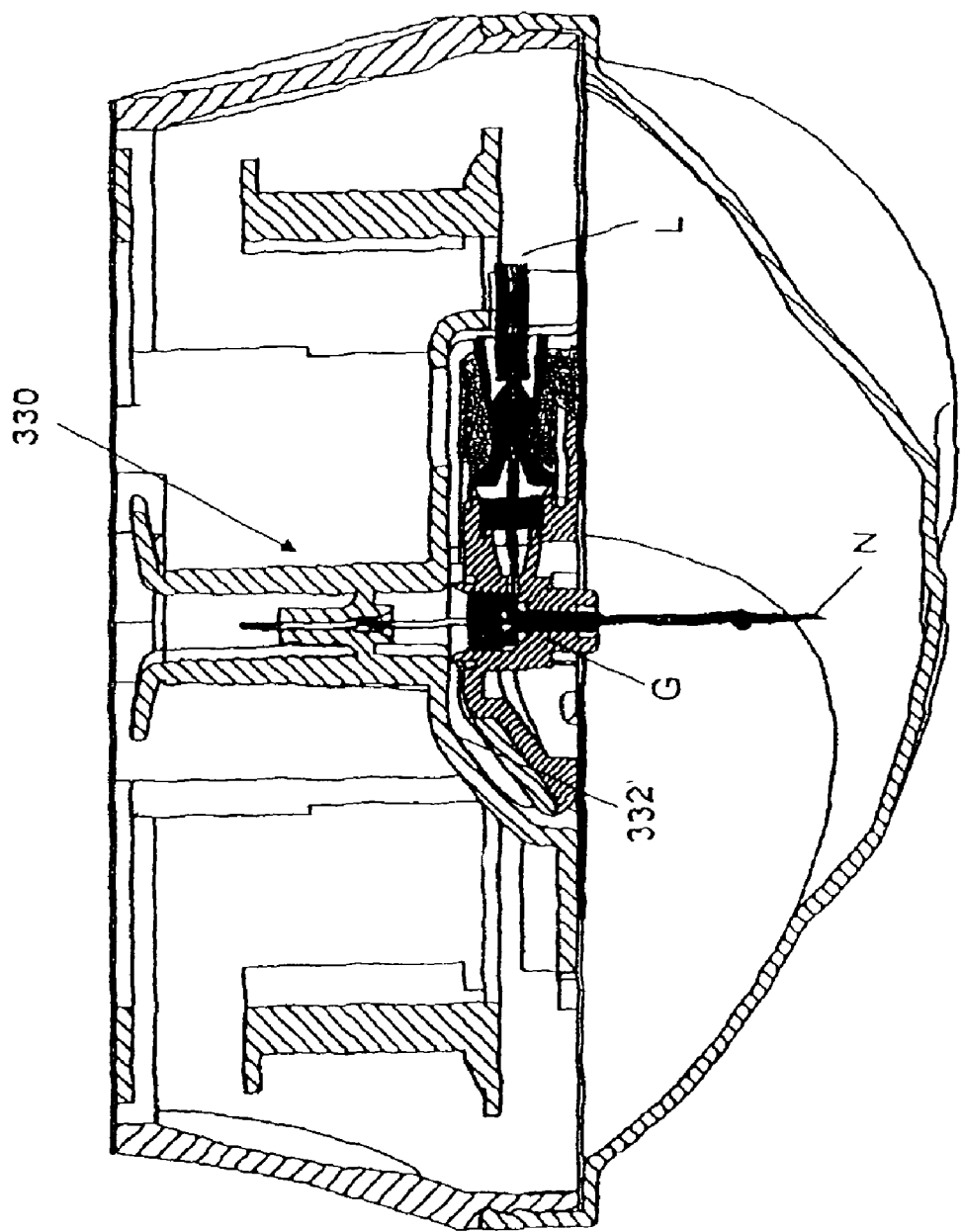
FIG. 24 shows the injector device of FIG. 19 with a glucose sensor.

A variety of further modifications and improvements to the automatic injector device unit of the present invention will be apparent to persons skilled in the art. Accordingly, no limitation on the invention is intended by way of the foregoing description and accompanying drawings, except as set forth in the appended claims. It is noted that the assembly may, depending on the design, be put on the market as such, i.e. with no further packaging being required Moreover, the injector device, provided with an insertion needle or not, is not exclusively suited for placing an infusion set but may also be used for placing a transcutaneous glucose sensor. FIG. 24 shows the injector device of FIG. 19 with the opposed sealed covers and with a glucose sensor housing G including a sensor needle N inserted into the patient by an insertion needle which is arranged in the plunger head recess 332' in lieu of an infusion set. The glucose sensor G may have a connecting cable L wound around the plunger 330 in the same manner as the infusion set tubing described above, or may have ports for connecting the glucose sensor to an external device for recording the glucose level of the patient.

The invention claimed is:

1. An injector device assembly comprising:
   a sterile insertion set with a housing and a hollow cannula;
   a device housing, said insertion set positioned removably from and within said device housing;
   a plunger received within said device housing for movement between an advanced position and a retracted position, said cannula being transcutaneously placed upon movement of the plunger from the retracted position to the advanced position, said insertion set being separable from said plunger;
   said device housing having a forward end defining a surface of placement against the skin of a patient; and
   a cover member covering an opening defined in said forward end and removably connected to a portion of said device housing, said cover member and said device housing assuring sterile conditions of said insertion set within said device housing prior to removal of said cover member.

2. The injector device assembly of claim 1, said injector device including an insertion needle extending through said hollow cannula and being in frictional engagement with said hollow cannula.

3. The injector device assembly of claim 1, said insertion set being an infusion set, said insertion set housing including an adhesive layer for adhering said insertion set housing to the skin of a patient.

4. The injector device assembly of claim 1, said insertion set being a glucose sensor.

5. The injector device assembly of claim 2, said insertion needle being secured to said plunger by a stable connection preventing loss of the insertion needle during use of the device.

6. The injector device of claim 5, said insertion needle being secured to said plunger by press-fit.

7. The injector device assembly of claim 1, including a trigger for releasably retaining said plunger in the retracted position, the trigger being operable to release the plunger for movement with a controlled force and speed toward the advanced position.

8. The injector device assembly of claim 1, said plunger including a support structure for reception and support of said insertion set, said support structure being removable from said insertion set while maintaining a transcutaneous placement of said insertion needle.

9. The injector device assembly of claim 1, indicia relating to the shelf life of said assembly being on said cover member.

10. The injector device assembly of claim 1, said plunger being in said advanced position prior to first time removal of said cover member.

11. The injector device assembly of claim 2, wherein said removable cover is member includes a hollow for receiving a part of said insertion needle when said plunger is in said advanced position.

12. The injector device assembly of claim 1, said cover being repositionable subsequent to removal of said insertion set.

13. The injector device assembly of claim 7, said trigger releasing said plunger by manual deformation of said housing.

14. The injector device assembly of claim 7, said insertion set including tubing for delivery of medication to said hollow cannula, said housing including an annular space for accommodating said tubing.

15. The injector device assembly of claim 1, said device housing including a releasable cover at a rearward end of said device housing.

16. The injector device of claim 15, said releasable cover at said rearward end being a membrane.

17. The injector device of claim 16, said releasable cover allowing through-flow of a sterilizing agent into said device housing with said insertion set.

18. The injector device assembly of claim 2, wherein said cover includes an upstanding cylinder for surrounding at least a portion of said insertion needle.

19. An injector device assembly comprising:
   a sterile insertion set having a housing and a hollow cannula;
   a device housing;
   a plunger slidably received within said device housing for movement between an advanced position and a retracted position, said cannula being transcutaneously placed upon movement of the plunger from the retracted position to the advanced position;
   a spring for urging said plunger toward the advanced position;
   said device housing having a forward end defining a surface for placement against the skin of a patient; and
   a releasable cover member covering said forward end, said cover member and said device housing assuring sterile conditions of said insertion set within said device housing prior to removal of said cover member;
   wherein said spring comprises a number of individual, flexible plastics strips extending around a respective part of the periphery of the plunger, in a space between the plunger and the device housing, each strip being connected with the plunger and with the device housing.

20. The injector device assembly of claim 19, wherein said strips are integrally molded with said plunger and said device housing.

21. The injector device assembly of claim 19, each strip being essentially planar and non-deformed when the plunger is in the advanced position.

22. The injector device assembly of claim 21, two strips extending in a common plane around a respective part of said periphery of said plunger, and two further strips extending in a second plane around a respective part of said periphery, in said advanced position of said plunger.

23. The injector device assembly of claim 19, wherein said strips and said plunger are molded as a unitary component, said unitary component being connected to said device housing.

24. An injector device assembly, comprising:
- a sterile insertion set with a housing and a hollow cannula, a molded device housing, said insertion set positioned within said device housing for delivery of said sterile insertion set to a patient;
- a molded plunger received within the device housing for movement between an advanced position and a retracted position;
- a lock for releasably locking said plunger in said retracted position, said housing being manually deformable to effect release of said plunger;
- a spring for urging the plunger from the retracted position towards the advanced position, said insertion set being separable from said plunger after placement of said cannula;
- said cannula being transcutaneously placed upon movement of the plunger from the retracted position to the advanced position;
- said housing having a forward end defining a surface for placement against the skin of a patient with the device housing in a predetermined orientation relative to the patient's skin; and
- a removable cover member covering an opening defined in said forward end and connected to a portion of said device housing;
- said cover member and said device housing assuring sterile conditions of said separable insertion set within said device housing prior to removal of said cover member.

25. The injector device assembly of claim 24 wherein the spring comprises a plurality of flexible plastic strips connected with the plunger and the housing, each strip extending around a respective part of the periphery of the plunger.

26. The injector device assembly of claim 25, wherein each of said strips is connected with the plunger and with the device housing, said connections being at different peripheral locations around the plunger.

27. The injector device assembly of claim 25, wherein each strip is essentially planar and non-deformed when the plunger is in the advanced position.

28. The injector device assembly of claim 25, wherein said strips and said plunger are molded as a unitary component, said unitary component being connected to said housing.

29. The injector device assembly of claim 25, wherein each of said flexible strips extends in a space between the plunger and the device housing.

30. The injector device assembly of claim 24, wherein said insertion set is an infusion set.

31. The injector device assembly of claim 24, wherein said insertion set is a glucose sensor.

32. The injector device assembly according to claim 24, wherein said insertion set includes an insertion needle that is substantially non-detachably secured to said plunger.

33. The injector device assembly of claim 32, wherein said insertion needle is hollow and has a lateral opening near said plunger.

34. The injector device assembly of claim 24, including manual engagement areas for the manual deformation of said housing to effect said release of said plunger.

35. The injector device assembly of claim 34, said manual engagement areas being diametrically opposed on said housing and being peripherally offset with respect to said lock.

36. The injector device assembly of claim 35 wherein said manual engagement areas are offset about 90°.

37. The injector device assembly of claim 35, said manual engagement areas being of fingertip size.

38. The injector device assembly of claim 24, said device housing including a releasable cover at a rearward end of said device housing.

39. The injector device of claim 38, said releasable cover at said rearward end being a membrane.

40. The injector device of claim 39, said releasable cover allowing through-flow of a sterilizing agent into said device housing with said insertion set.

41. A method for making an injector device assembly comprising the steps of:
- providing an injector device housing, said injector device housing having a movable plunger and providing an insertion set, said insertion set having an insertion set housing and a hollow cannula;
- placing said insertion set within said injector device housing;
- connecting at least one releasable cover to at least a portion of said injector device housing to seal said insertion set within said injector device housing, said cover comprising a membrane; and
- sterilizing said insertion set by flowing a sterilizing agent through said membrane into an interior of said injector device housing.

42. The method of claim 41, said device housing having a forward end defining a surface of placement against the skin of a patient with the device housing in a predetermined orientation relative to the patient's skin, said releasable cover member covering said forward end.

43. The method of claim 41, said device housing including a releasable cover at a rearward end of said housing.

44. An injector device for transcutaneously placing at least a portion of a cannula of a removable medical device through the skin of a patient, said injector device comprising:
- a generally cylindrically shaped housing having a cavity formed therein, said housing including a forward end, said forward end defining a generally planar surface for placement against the skin of the patient;
- a carrier member adapted for at least partial reception in said cavity, said carrier member comprising at least one piercing member substantially non-detachably secured to said carrier member;
- a drive for urging movement of said carrier member relative to said housing, said drive extending at least partially around at least a portion of said carrier member; and
- a releasable cover member covering said forward end, said cover member comprising an upstanding portion defining a bore;
- wherein said at least one piercing member is adapted to receive said removable medical device.

45. The injector device of claim 44, wherein said upstanding portion surrounds a portion of the at least one piercing member.

46. The injector device of claim 44, wherein said upstanding portion is cylindrically shaped.

47. The injector device of claim 44, wherein said cover member and said housing are configured to provide sterile conditions for the medical device prior to removal of said cover member.

48. An injector device assembly comprising:
- a sterile insertion set comprising a housing and a hollow cannula;
- a device housing having a cavity formed therein, said insertion set positioned removably from and within said device housing;
- a plunger having a piercing member connected to the plunger and positioned at least partially within said cavity, said piercing member extending at least partially through said cannula of said insertion set and said plunger configured to move said insertion set toward the skin of a patient; and a cover removably connected to a portion of said device housing, said cover accommodating a part of said piercing member, said cover and said device housing assuring sterile conditions of said insertion set within said device housing prior to removal of said cover.

49. The injector device assembly of claim 48, wherein said cover connects to and extends partially along a side wall at said forward portion of said device housing.

50. The injector device assembly of claim 48 wherein said cover is removably connected to said portion of said device housing by snap engagement.

51. A method for providing an injector device assembly having a sterile inertion set provided within an injector device housing, the method comprising:

proiding an injector device housing, said injector device housing having a movable plunger and a piercing member connected to the plunger;

providing an insertion set, said insertion set havig an insertion set housing and a hollow cannula;

placing said insertion set within said injector device housing so that said piercing member extends at least partially through said cannula;

connecting at least one removable cover to a portion of said injector device housing to cover an opening defined in said injector device housing and to seal said insertion set within said injector device housing, the cover accommodating a part of said piercing member; and strerilizing said insertion set within said injector device housing.

\* \* \* \* \*